United States Patent
Frank et al.

(10) Patent No.: US 12,293,840 B2
(45) Date of Patent: *May 6, 2025

(54) METHODS AND SYSTEMS FOR DETECTING ENVIRONMENT FEATURES IN IMAGES TO PREDICT LOCATION-BASED HEALTH METRICS

(71) Applicant: Urban Design 4 Health, Inc., Rochester, NY (US)

(72) Inventors: Lawrence D. Frank, San Diego, CA (US); James Chapman, Rochester, NY (US); Nicole Iroz-Elardo, Portland, OR (US); E-Sok Hong, Seoul (KR)

(73) Assignee: Urban Design 4 Health, Inc., Rochester, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/111,555

(22) Filed: Feb. 18, 2023

(65) Prior Publication Data

US 2023/0207135 A1    Jun. 29, 2023

Related U.S. Application Data

(63) Continuation of application No. 16/119,829, filed on Aug. 31, 2018, now Pat. No. 11,587,683.

(51) Int. Cl.
*G16H 50/30*   (2018.01)
*G06V 10/25*   (2022.01)
(Continued)

(52) U.S. Cl.
CPC ............. *G16H 50/30* (2018.01); *G06V 10/25* (2022.01); *G06V 10/764* (2022.01); *G06V 10/82* (2022.01); *G06V 20/176* (2022.01)

(58) Field of Classification Search
CPC ............................. G16H 50/30; G06V 20/176
See application file for complete search history.

(56) References Cited

U.S. PATENT DOCUMENTS

| | | |
|---|---|---|
| 8,738,422 B2 | 5/2014 | Lerner et al. |
| 8,892,455 B2 | 11/2014 | Lerner et al. |

(Continued)

FOREIGN PATENT DOCUMENTS

| | | |
|---|---|---|
| WO | WO 01/80099 | 10/2001 |
| WO | WO 2014/144730 | 9/2014 |

OTHER PUBLICATIONS

Schootman, M et al. "Emerging technologies to measure neighborhood conditions in public health: implications for interventions and next steps." International journal of health geographics vol. 15,1 20. Jun. 23, 2016 (Year: 2016).*

(Continued)

*Primary Examiner* — Jonathan Ng
*Assistant Examiner* — Benjamin L. Hanks
(74) *Attorney, Agent, or Firm* — Brandon N. Sklar; The Law Office of Brandon N. Sklar

(57) ABSTRACT

Various aspects described herein relate to a location-based and population-based health metric processes. In one example, a computer-implemented method for generating one or more predicted health metrics for a location includes receiving a request to assess the one or more health metrics associated with the location, and identifying at least one current or future built, social, or natural environment parameter associated with the location. The method may further include calculating one or more predicted health metrics associated with the location based upon at least one of the current or future built, social, or natural environment parameters associated with the location, monetizing the healthcare (Continued)

costs of the predicted health metrics and displaying the one or more predicted health metrics and costs.

21 Claims, 11 Drawing Sheets

(51) Int. Cl.
    *G06V 10/764*    (2022.01)
    *G06V 10/82*    (2022.01)
    *G06V 20/10*    (2022.01)

(56) References Cited

U.S. PATENT DOCUMENTS

| | | | |
|---|---|---|---|
| 2002/0010572 A1 | 1/2002 | Orton et al. | |
| 2013/0046586 A1 | 2/2013 | Lerner et al. | |
| 2014/0324395 A1* | 10/2014 | Silverman | G06N 5/04 703/1 |
| 2015/0347872 A1* | 12/2015 | Taylor | G01C 11/06 382/224 |
| 2015/0356099 A1 | 12/2015 | Targonski et al. | |
| 2016/0292626 A1 | 10/2016 | Green et al. | |
| 2017/0068782 A1 | 3/2017 | Pillai et al. | |
| 2018/0191867 A1* | 7/2018 | Siebel | G06F 8/35 |

OTHER PUBLICATIONS

Naik et al., Cities Are Physical Too: Using Computer Vision to Measure the Quality and Impact of Urban Appearance, American Economic Review: Papers and Proceedings, 2016, pp. 128-132. (Year: 2016).*

Naik et al., Streetscore—Predicting the Perceived Safety of One Million Streetscapes, 2014 IEEE Conference om Computer Vision and Pattern Recognition Workshops, 793-799, 2014 (Year: 2014).*

Xiao et al., Multiple View Segmentation for Street View Images, 2009 IEEE 12th International Conference on Computer Vision (ICCV)). (Year: 2009).*

Maizlish, Neil, et al., "Health and greenhouse gas mitigation benefits of ambitious expansion of cycling, walking, and Transit in California," Journal of Transport and Health, 6, 490-500 (2017).

Phillips et al., "Online versus in-person comparison of Microscale Audit of Pedestrian Streetscapes (MAPS) assessments: reliability of alternate methods," Int J Health Geogr 16, 27 (Available online Aug. 4, 2017).

Zhu, Wenfei, et al., "Reliability between online raters with varying familiarities of a region Microscale Audit of Pedestrian Streetscapes (MAPS)," Landscape and Urban Planning, 167, 240-248 (Available online Jul. 14, 2017).

Kurka, Jonathon M., et al., "Comparison of field and online observations for measuring land uses using the Microscale Audit of Pedestrian Streetscapes (MAPS)," Journal of Transport and Health, 3, 278-286 (2016).

Heat, Health economic assessment tool, WHO/Europe, webpage, old.heatwalkingcycling.org, 2014.

Woodcock, James, et al., "Health Impact Modelling of Active Travel Visions for England and Wales Using an Integrated Transport and Health Impact Modelling Tool (ITHIM)," PLoS One, vol. 8, Issue 1, 1-17 (2013).

Cain et al., "Development and reliability of a streetscape observation instrument for international use: MAPS-global," International Journal of Behavioral Nutrition and Physical Activity (2018) 15:19, https://doi.org/10.1186/s12966-018-0650-z.

Cain et al., "Contribution of Streetscape Audits to Explanation of Physical Activity in Four Age Groups Based on the Microscale Audit of Pedestrian Streetscapes (MAPS)," Soc. Sci. Med. Author manuscript; available in PMC Sep. 1, 2015; Published in final edited form as: *Soc Sci Med*. Sep. 2014; 116: 82-92. doi:10.1016/j.socscimed. 2014.06.042.

Ulmer, Jared M., et al., "Application of an evidence-based tool to evaluate health impacts of changes to the built environment." *Can J Public Health* 2015;106(1)(Suppl. 1):eS26-eS32.

Chow, Clara K., "A Novel Method to Evaluate the Community Built Environment Using Photographs—Environmental Profile of a Community Health (EPOCH) Photo Neighbourhood Evaluation Tool." PLoS One. 2014; 9(11): e110042. Published online Nov. 4, 2014. doi: 10.1371/journal.pone.0110042.

Duby, A. "Deep Learning the City: Quantifying Urban Perception at a Global Scale." European Conference on Computer Vision, ECCV 2016: Computer Vision-/ECCV 196-212.

Scott Weich, Elizabeth Burton, Martin Blanchard, Martin Prince, Kerry Sproston, Bob Erens, It environment: validity of a site survey instrument for use in urban settings, Health & Place, vol. 7, Issue 4, 2001, pp. 283-292, ISSN 1353-8292, https://doi.org/10.1016/S1353-8292(01)00019-3. (https://www.sciencedirect.com/science/article/pii/S1353829201000193).

Frank, L.D., et al., "The Development of a Walkability Index: Application to the Neighborhood Quality of Life Study." 2006 British Journal of Sports Medicine. 44, pp. 924-933.

Miller, D.K., "Using google street view to audit the built environment: inter-rater reliability results." Ann. Behav. Med. 45(1), 108-112 (2013).

Schoner J., et al., Bringing health into transportation and land use scenario planning: Creating a National Public Health Assessment Model (N-PHAM). 2018. Journal of Transportation and Health 10 (2018) 401-418.

Pikora TJ, et al., "Neighborhood environmental factors correlated with walking near home: Using SPACES." Medicine and Science in Sports and Exercise. Apr. 2006; 38(4):708-714. DOI: 10.1249/01. mss.0000210189.64458.f3. PMID: 16679987.

Day K, et al., "The Irvine-Minnesota inventory to measure built environments: development." Am J Prev Med. 2006; 30(2):144-152. doi:10.1016/j.amepre. Sep. 17, 2005.

Cerin, Ester, et al., Neighborhood Environment Walkability Scale. Medicine & Science in Sports & Exercise. Med. Sci. Sports Exerc., vol. 38, No. 9, pp. 1682-1691, 2006.

\* cited by examiner

METHODS AND SYSTEMS FOR DETECTING ENVIRONMENT FEATURES IN IMAGES TO PREDICT LOCATION-BASED HEALTH METRICS

RELATED APPLICATION

The present application is a continuation of U.S. patent application Ser. No. 16/119,829, which was filed on Aug. 31, 2018, is assigned to the assignee of the present patent application, and is incorporated by reference herein.

FIELD OF TECHNOLOGY

Aspects of the present disclosure generally relate to location-based and population-based health metric processes, and more particularly, to methods and systems for collecting, analyzing and manipulating built, social, and/or natural environmental parameters to predict health-related metrics or outcomes at various geographic scales.

BACKGROUND

For urban planners, developers, health insurance companies and elected officials who make decisions about land use and/or transportation policies, plans and investments; public health is a topic having a broad array of benefits, drawbacks and trade-offs that can be weighed in order to adequately and strategically inform such decisions. Indeed, decision-makers are often tasked with selecting a policy or planning development that will advance social, economic or policy goals at a cost to other competing goals.

In real world scenarios with finite resources and land, careful thought should be given to land development and investments to effectively maximize desirable economic, social and health benefits while minimizing the requisite costs. However, this task is complicated by the fact that the parameters used to calculate these benefits and costs are often based upon numerous variables, complicating the analysis and making it difficult to predict outcomes. Current technologies provide limited options for collecting, analyzing, and validating parameters related to economic, social and health benefits associated with land use, zoning and development. Moreover, the data necessary to make informed decisions about economic, social and health issues associated with land use, zoning, and development is highly fragmented and often contains inaccuracies which can have a negative impact on the decision-making process. Disadvantageously, current technologies lack intelligent, efficient, and reliable tools and mechanisms for collecting, validating, and analyzing built, social and environmental factors and developing environmental measures, land use plans, and policies that maximize economic, social, and health benefits.

BRIEF DESCRIPTION OF THE DRAWINGS

In order to describe the manner in which the above-recited and other advantages and features of the disclosure can be obtained, a more particular description of the principles briefly described above will be rendered by reference to specific embodiments thereof which are illustrated in the appended drawings. Understanding that these drawings depict only exemplary embodiments of the disclosure and are not therefore to be considered to be limiting of its scope, the principles herein are described and explained with additional specificity and detail through the use of the accompanying drawings in which.

DETAILED DESCRIPTION

Figure 1:
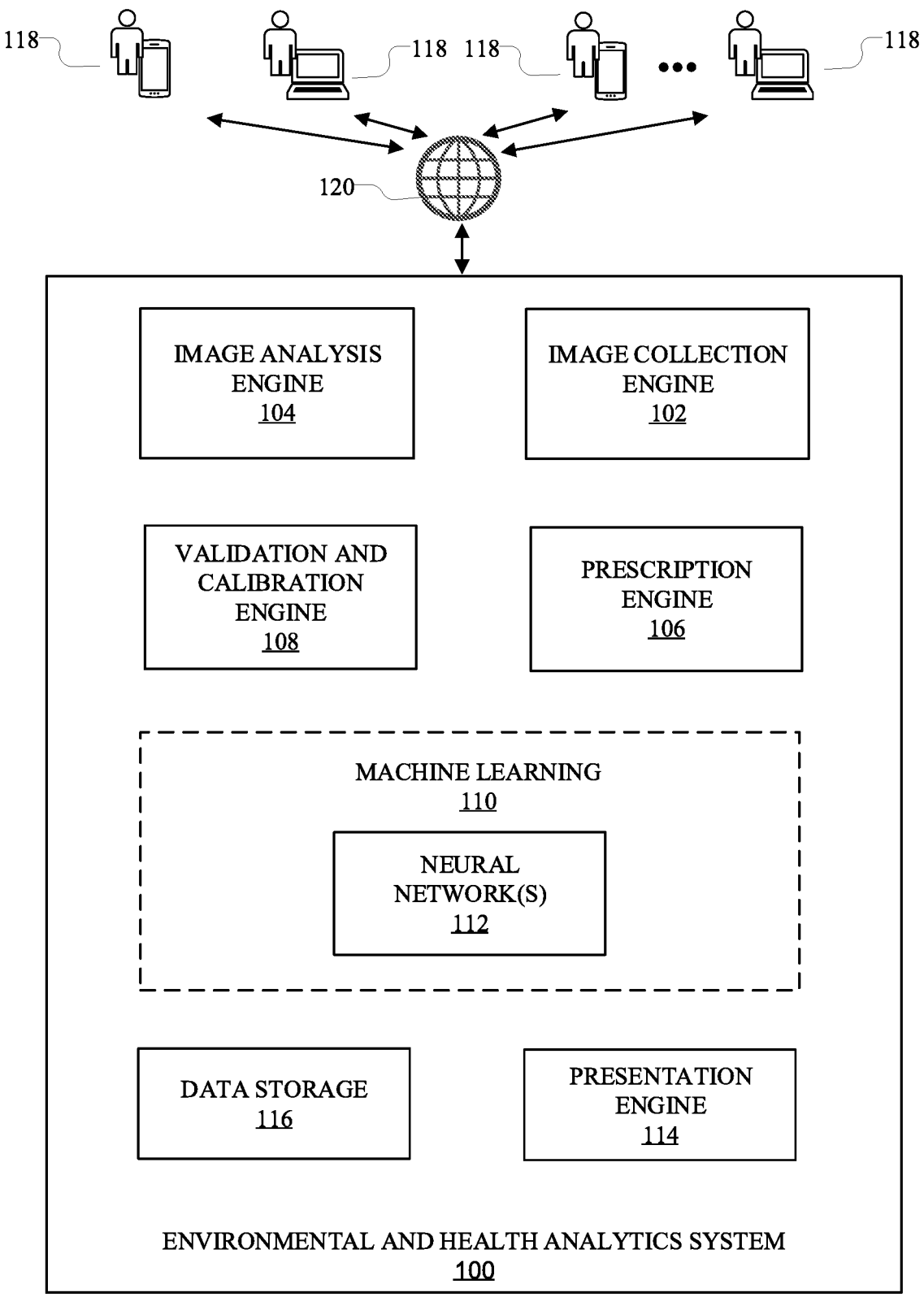
FIG. 1 illustrates an example environmental and health analytics system which can be implemented to collect environmental parameters for one or more locations, predict health-related outcomes or other metrics for the one or more locations, identify changes to one or more environments, and/or prescribe measures for improving a given health-related outcome and associated healthcare cost.

Various embodiments of the disclosure are discussed in detail below. While specific implementations are discussed, it should be understood that this is done for illustration purposes only. A person skilled in the relevant art will recognize that other components and configurations may be used without parting from the spirit and scope of the disclosure. Thus, the following description and drawings are illustrative and are not to be construed as limiting. Numerous specific details are described to provide a thorough understanding of the disclosure. However, in certain instances, well-known or conventional details are not described in order to avoid obscuring the description. References to one or an embodiment in the present disclosure can be references to the same embodiment or any embodiment; and, such references mean at least one of the embodiments.

Reference to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others.

The terms used in this specification generally have their ordinary meanings in the art, within the context of the disclosure, and in the specific context where each term is used. Alternative language and synonyms may be used for any one or more of the terms discussed herein, and no special significance should be placed upon whether or not a term is elaborated or discussed herein. In some cases, synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any example term. Likewise, the disclosure is not limited to various embodiments given in this specification.

Without intent to limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, technical and scientific terms used herein have the meaning as commonly understood by one of ordinary skill in the art to which this disclosure pertains. In the case of conflict, the present document, including definitions will control.

Additional features and advantages of the disclosure will be set forth in the description which follows, and in part will be obvious from the description, or can be learned by practice of the herein disclosed principles. The features and advantages of the disclosure can be realized and obtained by means of the instruments and combinations particularly pointed out in the appended claims. These and other features of the disclosure will become more fully apparent from the following description and appended claims, or can be learned by the practice of the principles set forth herein.

Overview

The disclosed technologies address the foregoing, unmet needs in the art by providing tools and strategies that for integrating quantitative analyses of built environment, social environment (e.g., demographic) and natural environment parameters into scenario planning tools to predict health outcomes and economic metrics. In some aspects, scenario tools according to the disclosure allow a user to generate models in order to evaluate potential health outcomes (or other metrics) associated with land use policies and/or development (e.g., by identifying built, social and/or environmental parameters that will optimize a selected health outcome in a given location). The tools described herein can be used to calculate economic benefits (or costs) associated with health outcomes that are predicted to result from changes to the built, social and/or environmental parameters associated with a given location. Accordingly, the present disclosure provides tools that can used to analyze and model a complex dataset in order to promote effective decisions regarding land use and development, to maximize desirable health outcomes and economic benefits (or to minimize costs), and to provide various other benefits as further described and illustrated herein.

The tools herein can include an automatic environmental auditing tool, which can be validated and calibrated using environmental audit data from human inputs around the world. The approaches herein also provide an evidence-based prescriptive tool to further improve specific environments, such as urban environments, for enhancing human health and wellbeing. A smart urban analytics program can be implemented for developing a next-generation environmental auditing tool and informing future policies and practices to promote healthier and more active living.

In some aspects, automatization of neighborhood environmental audits can enable users (e.g., urban planners, health practitioners, policy makers, etc.) to identify environmental features (e.g., houses, shops, trees, roads, sidewalks, bike paths, etc.) that may influence walking/bicycling behavior. The system can extract neighborhood images from the Internet, and apply a set of computer vision and machine learning technologies to automate identification and parsing of environmental objects.

Self-validation and calibration of computerized measures can be implemented based on real human inputs. Users can check the validity of the automatized measures and calibrate the measures to match real human inputs. The validation and calibration can done by calculating the similarity score between computerized audit scores and human-derived audit scores from a database of environmental audit data.

Evidence-based prescriptive tools can improve environments for healthier living. For example, a prescription tool can calculate a deficiency score of environmental features. The deficiency score can be calculated by measuring the quality and quantity of urban features that promote human health, such as trees, sidewalks, and streetlights. Based on the deficiency score, the tool can generate appropriate prescriptions to improve specific environmental features that enhance health and wellbeing.

The following description presents a simplified summary of several aspects of the disclosure in order to provide a basic understanding of the technologies described herein. This summary is not an extensive overview of all contemplated aspects, and is not intended to either identify key or critical elements of all aspects or delineate the scope of any or all aspects. Its purpose is to present some concepts of one or more aspects in a simplified form as a prelude to the more detailed description that is presented later.

In a first example, a computer-implemented method for generating health metrics for a location is provided. Such methods can include: (a) receiving a request to predict one or more health metrics associated with a location; (b) identifying at least one current built, social and/or natural environment parameter associated with the location; (c) calculating one or more predicted health metrics associated with the location based upon the at least one current built, social and/or natural environment parameter associated with the location; and (d) displaying the one or more predicted health metrics associated with the location.

In some example aspects, methods are provided for modeling potential changes to the built environment or other parameters associated with a given location (e.g., allowing a user to evaluate potential development or policy changes). Such methods can include: (a) receiving input including at least one new or modified built environment parameter associated with the location, and calculating one or more predicted health metrics associated with the location based upon the new or modified built environment parameter; (b) calculating one or more economic benefits resulting from a change in the predicted health metrics associated with the location based upon the new or modified built environment parameter; and (c) optionally, displaying the calculated economic benefit(s).

In some example aspects, methods can further include: (a) receiving input including a cost associated with the at least one new or modified built environment parameter and/or an estimated change in health care costs resulting from changes in the predicted health metrics associated with the location as a result of the at least one new or modified built environment parameter; and (b) displaying one or more costs or benefits resulting from the at least one new or modified built environment parameter.

In some examples, the predicted health metric for the location can include: (a) physical activity from travel and/or recreation; (b) body mass index; (c) rate of obesity and/or overweight; and/or (d) at least one health outcome. The health outcome can include a likelihood to have a cardiovascular disease, hypertension, type-2 diabetes, a mental health issue, and/or any other health condition. In some cases, the predicted health metric can a mean or median value for a typical resident or subpopulation of the location. Moreover, the location can be one or more census block groups, neighborhoods, boroughs, precincts, communities, geographic locations, etc.

In some examples, a method can include calculating a population-weighted aggregation of predicted health metrics for (a) all of the census block groups neighborhoods, boroughs, precincts, etc., associated with one or more locations; (b) a subset of the neighborhoods, boroughs, or precincts; and/or (c) a user-selected subset of the neighborhoods, boroughs, or precincts. The method can further include displaying the population-weighted aggregation of predicted health metrics via a computing display device. In some cases, one or more of the predicted health metrics associated with a location can be displayed in a tabular and/or geographic form.

In some aspects, the at least one current, new or modified built environment parameter can include a residential density, an intersection density, a retail floor area ratio, a land use mix, a transit proximity, a walkability metric, a regional accessibility, and/or a pedestrian environment. Moreover, the at least one built environment parameter can include a parameter associated with a regional accessibility, a walkability, and/or a pedestrian environment.

In some aspects, the at least one social parameter can include a gender, a race/ethnicity, an age, a number of vehicles owned per household, an income, housing and transportation costs per year per household, a distance to parks, and/or ozone concentration. Moreover, the at least one natural environment parameter can include an area of developed open space, a percent land area with tree canopy coverage, an ozone concentration, and/or a distance to parks.

In some aspects, the at least one current built, social and/or natural environment parameter associated with the location can be identified by accessing a local database or received from a remote electronic source.

In some aspects, a calculated economic benefit can include direct, indirect, and/or induced health effects predicted by an econometric analysis, a cost-of-illness calculation that accounts for direct health care costs and indirect productivity costs, input-output modeling, a value of statistical life methodology, and/or directly measured relationships between built environment parameters and health care or productivity costs.

In some examples, the method can further include: receiving one or more new or modified built, social and/or natural environment parameters selected by a user; generating at least one scenario that includes a model of the location based upon the new or modified built, social and/or natural environment parameters selected by the user; calculating one or more predicted health metrics associated with the location modeled in the scenario; and optionally displaying the one or more predicted health metrics associated with the location modeled in the scenario. In some cases, a plurality of scenarios can be generated and predicted health metrics can be calculated and displayed for each scenario.

In some examples, the method can further include: calculating one or more economic benefits resulting from changes to the predicted health metrics associated with the location modeled in the scenario, and displaying (i) at least one cost and/or benefit associated with the location based upon a user-provided budget to fund the new or modified built, social and/or natural environment parameters; and (ii) an estimated change in health care costs resulting from the changes in the predicted health metrics associated with the location modeled in the scenario. In some aspects, the scenario can include a model of the location under current conditions or potential conditions selected by the user.

In still further aspects, the disclosure provides computer-implemented methods for optimizing health metrics for a location. In some cases, an example method can include: (a) receiving a request to optimize one or more health metrics and/or economic benefits associated with a location; (b) generating at least one scenario which includes a model of the location based upon one or more selected or constrained built, social and/or natural environment parameters; (c) selecting an optimal scenario that maximizes the one or more health metrics and/or economic benefits associated with the location; and (d) displaying the one or more predicted health metrics or economic benefits associated with the location and/or the optimal scenario's built, social and/or natural environment parameters.

In some aspects, the optimal scenario is selected by a routine that includes: (a) a global optimization of a health metric or economic benefit metric with all modifiable built, social, and/or natural environment parameters; or (b) an optimization of a health metric or economic benefit based upon user-selected restrictions including an identification of at least one built, social, and/or natural environment parameter associated with the location which can be modified by the optimization routine and/or a requirement to maximize one or more user-specified health metrics while minimizing user-provided or predicted implementation costs associated with modifications to the built environment.

In still further aspects, the disclosure provides systems comprising an electronic memory and at least one processor configured to perform any of the methods described herein. The disclosure also provides non-transitory computer readable media storing computer-executable instructions for performing any of the methods described herein.

DESCRIPTION OF EXAMPLE EMBODIMENTS

Figure 9:
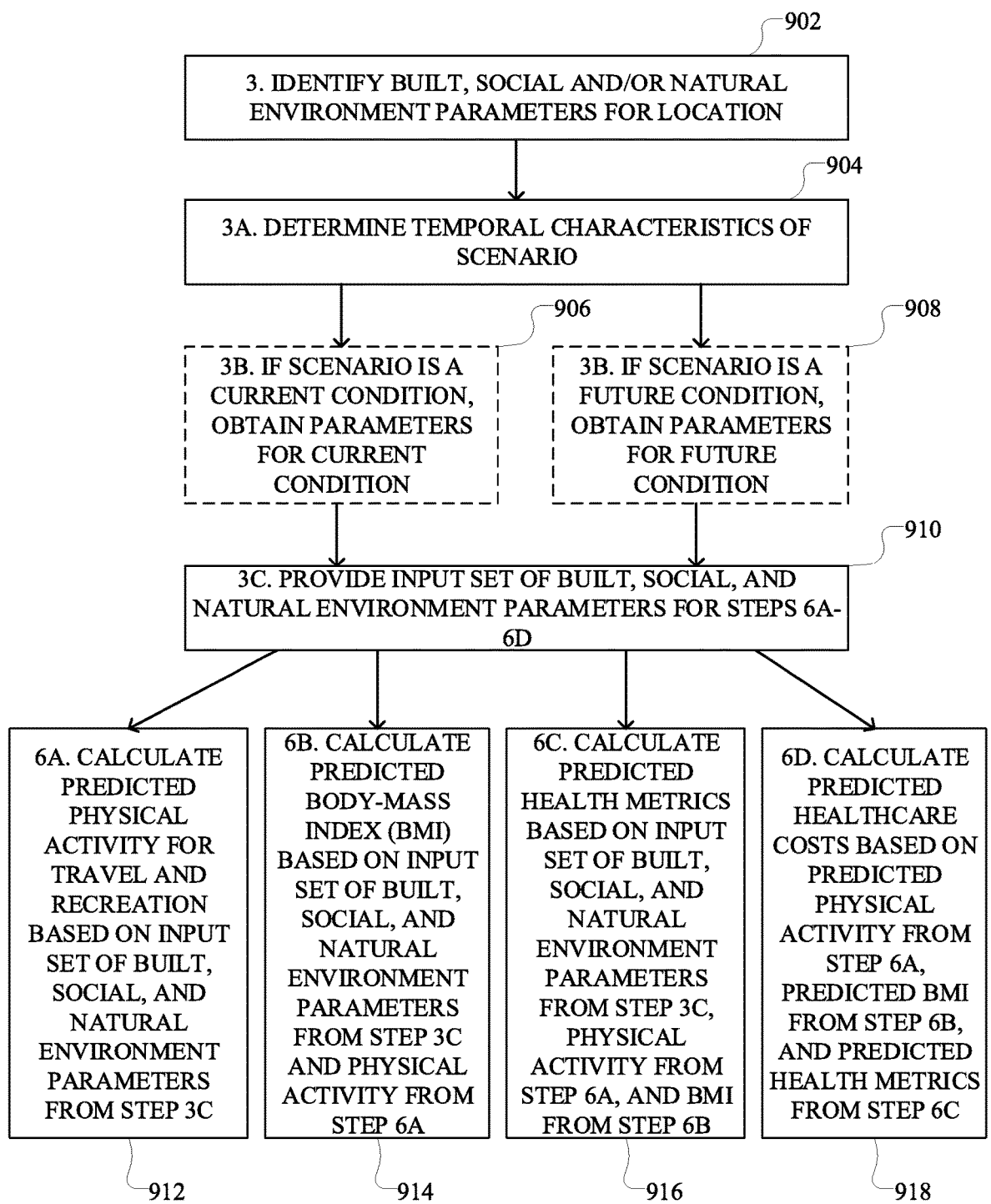
FIG. 9 illustrates a flow diagram of example methods of identifying input metrics and calculating health output metrics.
Figure 10:
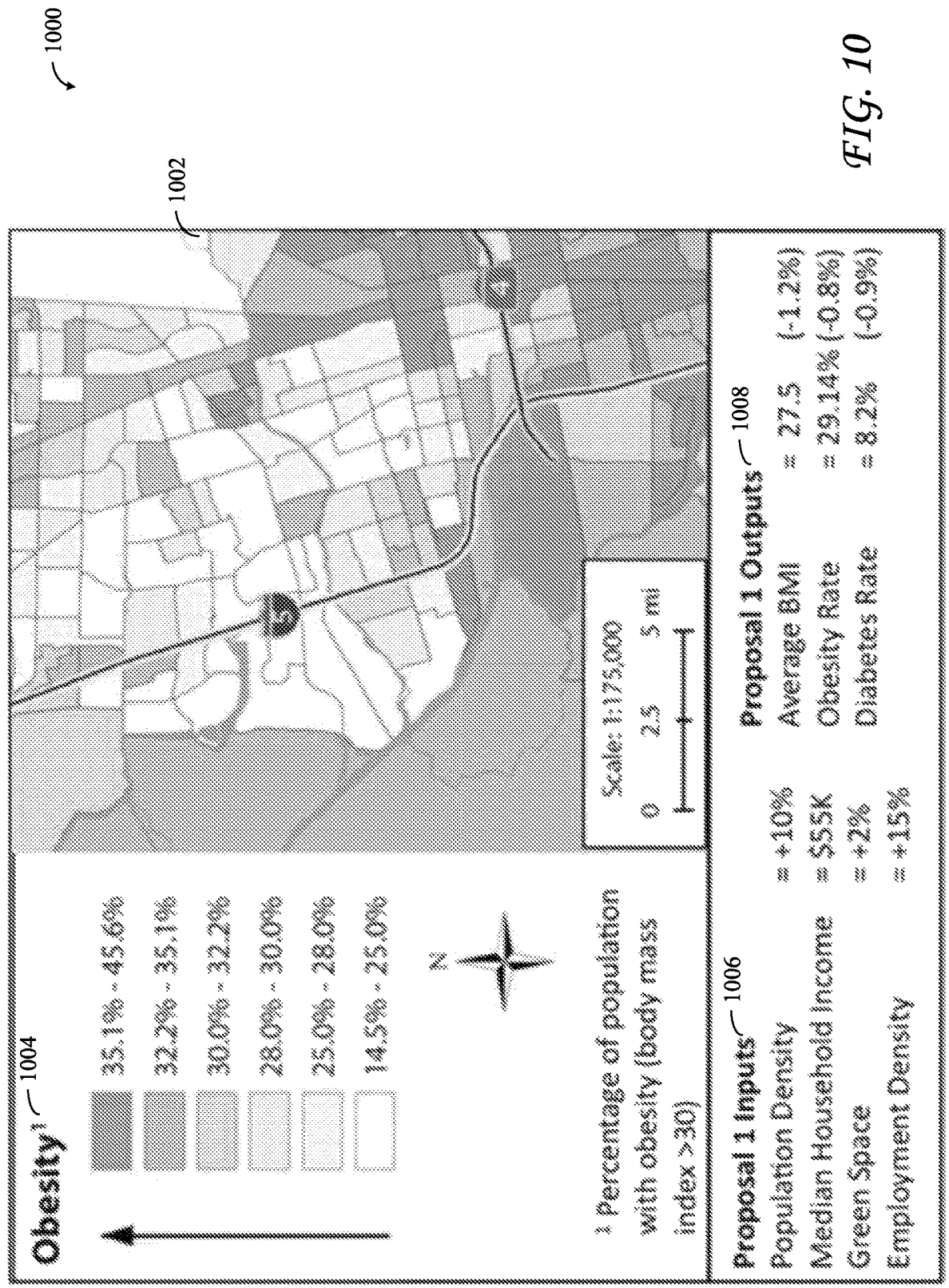
FIG. 10 illustrates an example output display depicting a map associated with a location and various environment and health parameters associated with the location.
Figure 11:
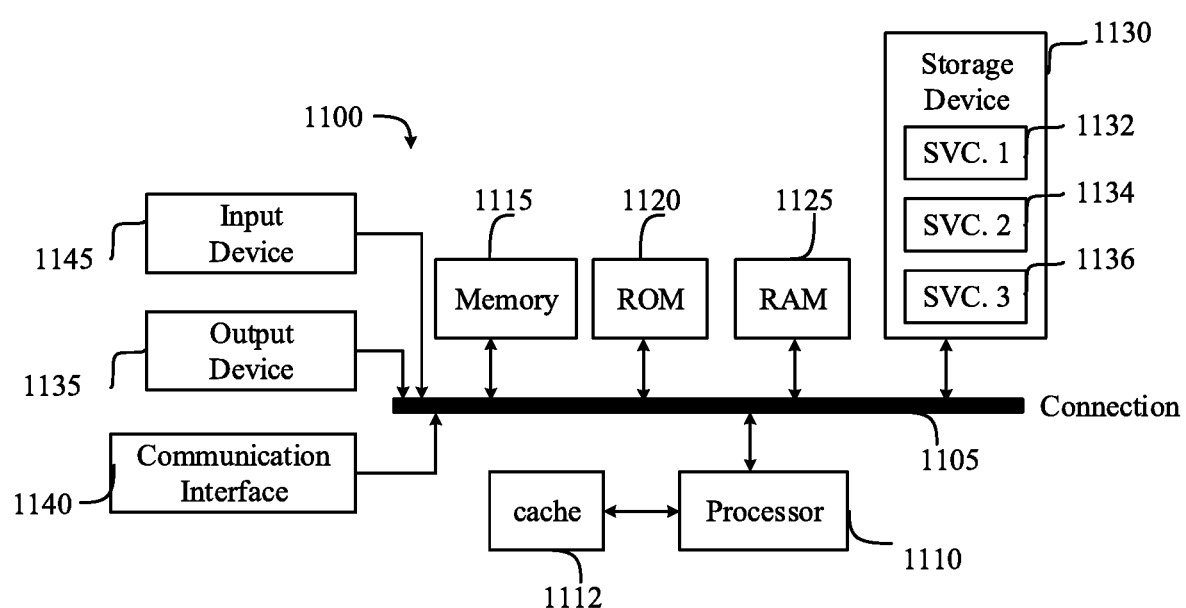
FIG. 11 illustrates an example computing device in accordance with various embodiments.

The disclosed technologies provide systems, methods, and computer-readable media for integrating quantitative analyses of built, social and natural environment parameters into scenario planning tools to predict health outcomes and economic metrics. The disclosed technologies also provide prescriptive tools for enhancing health and wellbeing through automatic detection and deficiency scoring of urban environmental features. The present technologies will be described in the following disclosure as follows. The disclosure begins with an introductory discussion of example planning and predictive tools for calculating health outcomes and costs and generating environment recommendations. A discussion of example methods and tools for automating environmental auditing procedures, validating and calibrating computerized environmental measurements, generating prescriptions to implement specific urban features, and predicting health-related parameters and metrics, as shown in FIGS. 1-10 will then follow. The discussion concludes with a description of an example computing device architecture, as illustrated in FIG. 11, including example hardware components suitable for running computer tools and performing computing operations in accordance with the present disclosure.

The disclosure now turns to the introductory discussion of example planning and predictive tools for calculating health outcomes and costs and generating environment recommendations.

As previously explained, the approaches herein can assist urban planners and other decision-makers that develop and implement policies, and provide development strategies using machine learning tools and location-based data and routines (e.g., geographic information system (GIS) locational data and routines). The term "built environment" as used herein refers to a term of art in urban planning referring to buildings and/or other man-made structures.

The approaches herein can provide methods, system, and/or planning tools for producing health behavior(s), health outcome(s), health metrics, and evidence-based prescriptive tools for improving urban environments and enhancing human health and wellbeing. In addition to built environment measurements, health measures can draw upon social environment (e.g., demographics) and/or natural environment measurements. In some aspects, phenomena such as greenhouse gas emissions, walkability, and/or physical activity can be evaluated or estimated to predict or generate health-related parameters, metrics or outcomes at one or more geographic scales. For example, health-related parameters can take into account factors such as surrounding sidewalks, street connectivity, neighborhood safety, surroundings (e.g., buildings, greenery, parks, commercial establishments, gas stations, public transportation systems, schools, hospitals, police stations, uninhabited buildings, etc.), pedestrian volumes, visual enclosure (e.g., rate of access to the sky), living standards, satisfaction metrics, crime rates, etc.

Scenario planning tools can also be implemented to model various changes to built, social and/or environmental parameters (e.g., to optimize health outcomes, economic benefits or other metrics). For example, a user may evaluate how potential changes in community design might impact outcomes such as employment, transportation, energy use, land consumption, etc. Scenario planning tools can include GIS data and/or routines, machine learning functionalities (e.g., data collection, feature abstraction, data and/or feature analysis, predictive analysis, validity checks, etc.), and predictive equations, and may be used to assist national, regional and local planning efforts.

The scenario planning tools can allow local/regional governments or government agencies to analyze the impact of different land use scenarios. In some cases, the scenario planning tools can be used to integrate and/or extend existing urban design or planning methods or tools. For example, scenario planning methods can be integrated, in whole or in part, into existing scenario planning platforms or computer systems. While the disclosed planning tools and methods may be provided as a standalone software package, in some aspects, one or more features of the software tools and methods described herein may alternatively be incorporated into one or more larger software packages as an intermediary component. For example, one or more of the present methods may be used as a subroutine to calculate and/or optimize parameters for a given location (e.g., one or more cities) as part of a larger software package or computer tool that may, for example, provide scenario planning for a whole region (e.g., a state)

Various aspects described herein can implement methods, systems and/or tools to predict health-related outcomes and other metrics from a number of factors that may include built, social, and/or natural environment parameters. In some aspects, coefficients that are estimated using statistical analysis can be used to internally predict parameters, health outcomes or other metrics. For example, physical activity (e.g., transportation, exercise, or recreation) and/or body mass index may be predicted as a related health risk factor, and used to predict final health outcomes. In some examples, the predicted health outcomes or outputs can be prevalence rates (e.g., the rate of diabetes in the adult population, the rate of certain diseases of individuals in a particular area, crime rates, education rates, employment rates, obesity rates, etc.). The term "prevalence rate," as used herein refers to the number of people in a group with a new or old diagnosis, condition, or characteristic divided by the population of that group. For example, diabetes prevalence is 9% among U.S. adults older than 18, meaning that 9 out of 100 U.S. adults report having diabetes. In some cases, predicted health outcomes can be calculated for individuals, groups, and/or subgroups.

In some aspects, given a location (e.g., a street address), the disclosed strategies may identify one or more physical, social, and/or natural environment indicators, and may predict a related suite of population-based health metrics for the given location. In some cases, the disclosed process can be used for current conditions and/or applications for future scenarios at a variety of geographic scales (e.g., a neighborhood, a census tract, or a census block group).

In some example aspects, built, social, and/or environmental data can be manipulated to predict health-based outcomes at a small geographic scale. For example, the health-based outcomes may be one or more location-based population health metrics. A location and one or more physical, social, and/or natural environment parameters can be identified and used to predict or determine a related suite of population-based health metrics for the location. In some aspects, the disclosed strategies can be used as part of a generic land-use toolset (e.g., allowing a user to calculate various predicted metrics which may or may not include health-related outcomes). In other aspects, the present strategies can be incorporated into software that is specifically directed to health outcome prediction.

Smaller regions, such as geographic and/or politically-defined regions, can also be analyzed and/or modeled using the presently disclosed approaches. For example, the approaches herein can be used to analyze individual neighborhoods, boroughs or census tracts. The more granular analysis in this example can be advantageous in scenarios where an analysis of a greater area or region may be unsuitable. It is understood that the geographic unit or scales of locations analyzed using the present approaches will vary depending upon the intended application or implementation.

In some cases, a location selected for analysis can include an aggregate of multiple geographic and/or politically-defined regions (e.g., a location may include a plurality of census tracts, multiple towns or cities, etc.). These regions may be adjacent regions, but may be distributed or non-adjacent in other cases. Geographically remote areas may be included in a single location in some instances (e.g., neighboring towns separated by an unincorporated area). In some cases, the disclosed approaches can be applied to current condition(s). Moreover, the present approaches can also be used to model future scenarios. Future scenarios can include, without limitation, models that account for potential built environment changes (e.g., activity resulting from rezoning or subsequent development of a previously undeveloped plot of land), natural environment changes (e.g., health outcome effects in a location due to global warming), or social environment changes (e.g., demographic changes due to changes in land use policies).

In some example aspects, location-based and population-based health metrics can be used to estimate reduced health care expenditures and increased health productivity; direct, indirect and induced economic activity; costs and benefits; and/or relative trade-offs (e.g., costs/benefits) from one or more co-benefits such as the costs to implement the changes to environment, land or property values.

Location-based built, natural and social environment (e.g., demographic) parameters can also be used to calculate estimated environmental scores (e.g., walkability, accessibility, greenery, etc.). Such calculations may be based on current environmental parameters or future/potential parameters modeled for a given location.

In addition to using location-based and population-based health metrics, the disclosed approaches may incorporate health, safety and climate considerations (e.g., trips that are linked with energy, emissions, pollution and associated costs).

In some example aspects, the location-based and population-based health metrics can be modified to include a personal health metric that is customized to include personalized demographic and/or health factors. For example, the personalized demographic and/or health factors can include or provide a personal physical activity score and/or health score.

Metrics related to the pedestrian environment, also referred to as "pedestrian micro scales" (e.g., micro-geographic scales), can also be integrated in the environmental and/or health parameters implemented. For example, the location-based and population-based health metrics can include characteristics of the one or more micro scales, such as presence/absence of street lights, benches, curb cuts at intersections, traffic signals, marked crosswalks; width, condition and continuity of sidewalk; distance from sidewalk and height of buildings, including presence and location of windows; width of intersection crossings and roads between intersections; etc.

In some aspects, the present approaches can also use demographic or sub-demographic information or data. For example, the location-based and population-based health metrics may generate, provide, or include outcomes based on pre-specified populations, e.g., youth, elderly, or a pre-defined age group.

In some aspects, a user may select or provide a location (e.g., a neighborhood in New York City) and the disclosed technologies can populate a map of the given location by importing: (a) built environment parameter(s), (b) social environment (e.g., demographic) parameter(s), and/or (c) natural environment parameter(s). For example, "access to bike paths" can be one of the above-mentioned environment parameters. Health-related outcomes for individuals living at this location can also be predicted by applying various algorithms to one or more built, social, and/or natural environment parameters. For example, a location may have a built environment that provides more options for physical activity resulting in a predicted lower rate of morbidity for individuals living at the location (e.g., access to bike paths nearby may promote more exercise). In some implementations, a number of potential parameters can be accounted for to give a fine-tuned prediction.

In some examples, computer systems and/or machine learning tools can be implemented to predict location-based population health outcomes from built, natural, and/or social environment (e.g., demographic) parameters. For example, a computer system can obtain and process a request for a location assessment (e.g., from a user), estimate one or more travel behaviors (e.g., minutes spent in active and/or recreational travel), and predict one or more health outcomes (or other metrics) based upon a plurality of the built, natural, and/or social environment (e.g., demographic) parameters associated with the given location. In some cases, travel minutes and health metrics may be based upon the weights of the built, natural, social environment (e.g., demographic) parameters previously determined using an analysis of representative travel and/or health surveys. In another aspect, the computer system may return or display the health-based outcome(s) in a geographic and/or tabular form.

In some example aspects, a built environment parameter described herein can include a population density, street connectivity, and/or land-use mix. In another aspect, at least one additional built environment parameter may capture or indicate the availability of green space, transit, and/or other considerations related to the given location. In some examples, the built environment parameter(s) may be previously calculated and/or saved in a computer-readable medium or device (e.g., a computer memory), calculated in real time within a routine (e.g., a location health outcome routine), or provided by an end user (e.g., a real estate or urban planning professional).

In some aspects, social (e.g., demographic) parameters can include age(s), race(s), household income(s), gender(s), etc. In some examples, such parameters may be previously calculated and/or saved in a computer-readable medium or device (e.g., a computer memory), calculated in real time by software implementing the present approaches, or provided by the end user (e.g., a real estate or a urban planning professional).

In some aspects, the calculated health metric may be returned in tabular and/or geographic form as a single metric. The tabular and/or geographic presentation may identify the built, natural and/or social (e.g., demographic) environment parameter(s) used in the computation. The tabular and/or geographic form may be returned with comparisons of one or more health metrics assigned to at least one additional location. For example, the one or more health outcome metrics assigned to at least an additional location may further include a second health outcome metric calculated used for a larger geographic area (that encompass the requested/identified location), where the second health outcome metric is calculated by using a weighted average of the process for all locations within the larger geographic region. In some cases, the one or more health outcome metrics assigned to at least an additional location can include a health outcome metric for another similar and/or nearby location.

In some examples, a computerized program can be implemented to automate detection of urban features and offer environmental prescription to enhance health and wellbeing. Built and natural environment features play an important role in shaping human activity and perceptions, thus influencing human health and quality of life. Various strategies can be implemented to measure attributes of both objective and perceived neighborhood environment. One example strategy is a neighborhood environmental audit, which allows for quantifying various urban features known to influence human health and quality of life. In some cases, humans can be used to assist with environmental audits. However, one example difficulty with use of humans to complete the auditing process is that there are substantial time and costs associated with relying on humans. There are also potential biases caused by cognitive and personal differences among individuals.

To address these and other problems, the present technologies can implement computer vision and machine learning technology to automate the environmental auditing process and offer evidence-based environmental prescriptions. This approach can leverage already collected environmental audit data around the world to validate and calibrate the automatic tool. The wealth of such data can be used to successfully compare computerized measures against the audited measures based on human inputs. Furthermore, the approaches herein can provide a set of environmental prescriptions to enhance human health and wellbeing. The present technologies can offer health authorities and municipalities a cost-effective solution to assess neighborhood quality and inform policies and practices to enhance health and wellbeing for urban residents.

The environmental auditing process can implement various types of auditing procedures. For example, neighborhood walkability audits can capture perceived built environment features that are likely to influence walking behavior. A Neighborhood Environment Walkability Scale (NEWS) can capture individuals' perceptions of the neighborhood in terms of sidewalks, street connectivity, safety, surroundings, overall satisfaction, etc. The NEWS instrument can be used in different languages (e.g., English, Chinese, and Japanese) and for different population subgroups (e.g., adults and youth). The NEWS instruments can be adapted and translated for use in various countries with acceptable test-retest reliability and concurrent validity with respect to objective built environment measures. Detailed assessment of perceived neighborhood environment through the NEWS approach can be effective and useful to offer evidence-based policy recommendations to improve walkability and neighborhood quality of life.

However, there are many challenges in conducting a large-scale NEWS tool in a timely and a cost-effective manner. Accordingly, other approaches can be utilized to address some or all of the challenges faced by NEWS-based approaches. For example, other technologies such as Google Street View can offer options to supplement the actual field audit process. Instead of physically going to a site to conduct environmental audit, a web-based tool using Google Street View can allow people to browse through the neighborhood and conduct the auditing process in a web environment. However, these tools still require human labor and costs associated with having to rely on humans to rate the built environment according to predefined metrics. Because the environmental audit in such approach is still done by humans, cognitive differences and personal characteristics may influence the scoring results, potentially leading to errors and human biases. Moreover, people's perception about the environment can vary between different socio-economic groups and socio-cultural factors. Thus, it is challenging to develop a comparable metrics that can be applied across different population subgroups and to cover a larger geographic area.

The computerized tools and strategies herein can offer a feasible alternative to relying entirely on humans to evaluate built environment features. For example, computer vision and machine learning technology can be implemented to reduce or remove reliance on humans. For applications in the built environment audit, Google Street View images and similar technologies can be used to score safety and such measures can be validated based on crowd-sourced human inputs. Google Street View and similar technologies can also be used to detect pedestrian volumes and street-level urban greenery. Machine learning tools can be implemented to quantify visual enclosure, defined as a proportion of sky ahead the street and across the street. Although it is often difficult to validate such measures derived from computer tools, it is, however, possible to train computers to closely match the audit results and improve the machine's performance to simulate human-derived measures as closely as possible.

The approaches herein offer an automatic environmental auditing tool and allow for validating and calibrating the automated tool using environmental audit data from human inputs around the world. An evidence-based prescriptive tool can also be implemented to further improve the urban environments for enhancing human health and wellbeing. The analytics techniques herein can be applied to develop a next-generation environmental auditing tool and inform future policies and practices to promote healthier and more active living.

Automatization of Neighborhood Environmental Audits

The automatic environmental auditing tools herein allow users (e.g., urban planners, health practitioners, policy makers, etc.) to identify environmental features (e.g., house, shops, trees, roads, sidewalks, bike paths, etc.) that may influence walking/bicycling behavior based on environmental auditing methods. The system can extract neighborhood urban images from the Internet, and apply a set of computer vision and machine learning technologies to automate identification and parsing of urban environmental objects.

Self-Validation and Calibration of Computerized Measures

Users can check the validity of the automatized measures and the measures can be calibrated to match real human inputs. The validation and calibration can be done by calculating the similarity score between computerized audit scores and human-derived audit scores from a database of environmental audit data.

Evidence-Based Prescriptive Tool

A prescription tool to improve urban environments for healthier living can calculate deficiency scores of urban environmental features. A deficiency score can be calculated by measuring the quality and quantity of urban features that promote human health, such as trees, sidewalks, and streetlights, for example. Based on the deficiency score, this tool can offer users prescriptions to improve specific urban features that enhance health and wellbeing.

Monetization of Health Care Costs

The relationship between aggregate costs of disease and disease prevalence rates is such that average 'per case' (per person) costs are reported or can be calculated. Multiplying the number of cases by annual per case costs provides an estimate of the current costs associated with each disease of interest. The number of cases of various diseases can be calculated based on built, natural and social environment variable values for a given study area.

A scenario planning tool, as further described below, and/or a user can also specify a change/future scenario for which new health outcome values should be calculated. The number of avoided cases can then be defined as (1) all cases of disease at baseline or (2) the difference in expected cases between the future scenario and baseline. Various modeling approaches as well as specific methodological concerns that may be accounted for in the planning tool development process are addressed herein.

Modeling Approaches

The modeling process for monetizing health impacts from the built and natural environment and active transportation can include estimating census block group (CBG) level physical activity and health outcomes associated with multiple built, natural and social environment conditions/scenarios; applying a cost of illness (COI) to CBG-level disease counts; and/or comparing multiple scenarios to determine relative levels of health outcomes and costs.

Sources for Cost of Illness (COI) Estimates

COI estimates can be sourced from peer-reviewed literature and federal agency reports. For each disease endpoint, the COI literature can be searched and the most recent COI ascertained.

Addressing Comorbidities

COI studies seek to isolate the additional cost attributable to the disease of interest and thus control for common comorbidities. Care should be taken to understand study assumptions when summing multiple illnesses together in an application according to various aspects of the disclosure.

Choosing a Monetary Base Year

Because multiple COI studies with multiple base years may be applied, COI amounts can be standardized to a single year. In some examples, the Bureau of Labor Statistics (BLS) Consumer Price Index (CPI) Inflation Calculator can be applied. The CPI includes sub-categories including a medical category. The "medical care" portion of the index can be used to transform COI into a single base year.

Choosing a Geography to Aggregate

There is little literature to guide how costs vary across a region. Average costs across the U.S. (or if available, across a state) can be applied.

Applying Cost of Illness

Health outcome specific COI study results can be used. COI estimates can be adjusted to a common year using the general CPI Inflation Calculator provided by the U.S. for the Bureau of Labor Statistics. The relationship between aggregate cost and prevalence rates is such that average 'per case' costs are reported or can be calculated. Multiplying the number of cases by annual per case costs provides an estimate of the current costs associated with each disease for a given location.

In addition to individual medical cost savings, businesses also benefit from an increase in employee productivity from reduced illness attributable to increased physical activity. Those who are not active at least 150 minutes each week miss on average 0.63 days of work each year. Using the methodology for avoided healthcare expenditures, the number of fewer absentee days by an inactive person for each health district can be normalized on a "per mile walked" and "per mile biked" basis.

The results can be used as inputs to input/output models across industries to determine the wider economic impact. These models can be used to compute each worker's daily productivity (output per worker per day), which in turn can be combined with other multipliers and number of absentee days not taken to estimate total impacts.

The estimated absentee reduction value per rider mile can be based on the output per employee per day and the annual absentee days not taken per mile. The output per employee per day is an input/output model generated industry output per employee divided by the number of days worked.

The disclosure now turns to a description of example methods and tools for environmental auditing procedures, validating and calibrating computerized environmental measurements, generating prescriptions to implement specific urban features, and predicting health-related parameters and metrics. The examples and concepts described in the description below will be described with reference to the appended drawings and are intended as a description of various non-limiting configurations. The description below includes specific details for the purpose of providing a thorough understanding of various concepts. However, it will be apparent to those skilled in the art that these concepts may be practiced without certain details.

Several aspects of planning tools or routines will now be presented with reference to various systems and methods. These methods and systems will be described in the following detailed description and illustrated in the accompanying drawings by various blocks, modules, components, circuits, steps, processes, algorithms, etc. (collectively referred to as "elements"). These elements may be implemented using electronic hardware, as shown in FIG. 11, computer software, or any combination thereof. Whether such elements are implemented as hardware or software depends upon the particular application and design constraints imposed on the overall system.

FIG. 1 illustrates an example environmental and health analytics system 100 (hereinafter "system 100") which can be implemented to collect environmental parameters for one or more locations, predict health-related outcomes or other metrics for the one or more locations, and/or identify changes to one or more environments and which can be used to increase a given health-related outcome or other metric. For example, the system 100 can be used to predict a location-based population health outcome from measures of built, natural, and/or social (e.g., demographic) environment parameters. As will be further described below, the system 100 can computerized environment auditing tools which can implement machine learning technologies for collecting environment parameters; analyzing environment parameters; generating audit scores; generating recommendations or prescriptions for implementing environment features to improve health, wellbeing, and healthcare costs; etc.

In some examples, the system 100 can include an image collection engine 102. The image collection engine 102 can query, crawl, retrieve, and/or store environmental images from one or more sources, such as the Internet 120, for a designated geographic area/region or within a user-selected buffer. In some cases, the image collection engine 102 can obtain images for a geographic area from an Internet application or source such as GOOGLE STREET VIEW, and store any collected images on data storage 116 for current or future use and access.

Image analysis engine 104 can apply vision and machine learning technology 110 to identify specific environmental features in the images collected by the image collection engine 102. Non-limiting examples of environmental features can include houses, shops, benches, trees, roads, sidewalks, bike paths, streetlights, people, vehicles, fountains, parks, bodies of water, sunlight, crowds, empty spaces, traffic, animals, and/or any environmental features which may affect human activity and behavior such as walking or bicycling. In some cases, the image analysis engine 104 can implement neural network 112 to identify environmental features in images. The neural network 112 can allow the image analysis engine 104 to recognize objects in images, as further described with reference to FIG. 4.

The validation and calibration engine 108 can obtain environmental audit data from users 118 and use the environmental audit data from the users 118 to perform self-validation and/or self-calibration of computerized environmental audit measures generated by the system 100. For example, the users 118 can check the validity of automatically-generated environmental measures and calibrate such measures to match human inputs from the users 118. In some cases, the validation and calibration can be performed by calculating the similarity score between computerized audit scores generated by the system 100 and user-derived audit scores (e.g., audit scores from users 118). Computerized audit scores and/or user-derived audit scores can be stored in the data storage 116 for use and access by the system 100.

The system 100 can also include a prescription engine 106 that calculates and generates prescriptions for implementing specific environmental features that can improve environments, human health and wellbeing, and healthcare costs and efficiency. The prescription engine 106 can be an evidence-based computer tool for predicting or suggesting measures for healthier living. The prescription engine 106 can calculate deficiency scores of environmental features and use the deficiency scores to generate prescriptions for improving environmental features known or believed to improve health and wellbeing. In some cases, the deficiency scores can be calculated by measuring the quality and quantity of environmental features that promote health and wellbeing, such as, without limitation, trees, sidewalks, streetlights, bike paths, water resources, sunlight, etc.

A presentation engine 114 can use the data from prescription engine 106, as well as any other data collected or generated by the system 100 such as statistics or map information, to display environmental features, statistics, prescriptions, audit scores, healthcare costs, and/or other health or environment related data for one or more locations. For example, the presentation engine 114 can generate an interface or graphical view of such data for display at one or more display devices (e.g., local display device on the system 100 and/or remote display device on a different system). The presentation engine 114 can configure and/or format data for presentation based on user preferences, system preferences, system capabilities, type of data being presented, various available formatting options, etc. For example, the presentation engine 114 can format the data in tabular form, geographic or map form, as a chart or graph, in textual form, and/or any other graphical or animated form.

The data storage 116 can be used to store images from the image collection engine 102, features identified from the collected images, computerized and/or human audit scores, validation and/or calibration data or statistics, prescription data generated by the prescription engine 106, presentation data generated by the presentation engine 114, inputs from users 118, map or geographic data, logs, data and/or statistics obtained from the Internet 120, changes in environmental features or data, metadata, health and/or environmental metrics, information about environmental and/or health-related features, health and/or environmental goals for one or more locations, health and disease factors, disease prevalence rates, health/disease and environmental correlation data, cost and/or health impacts associated with one or more variables, etc.

Figure 2:
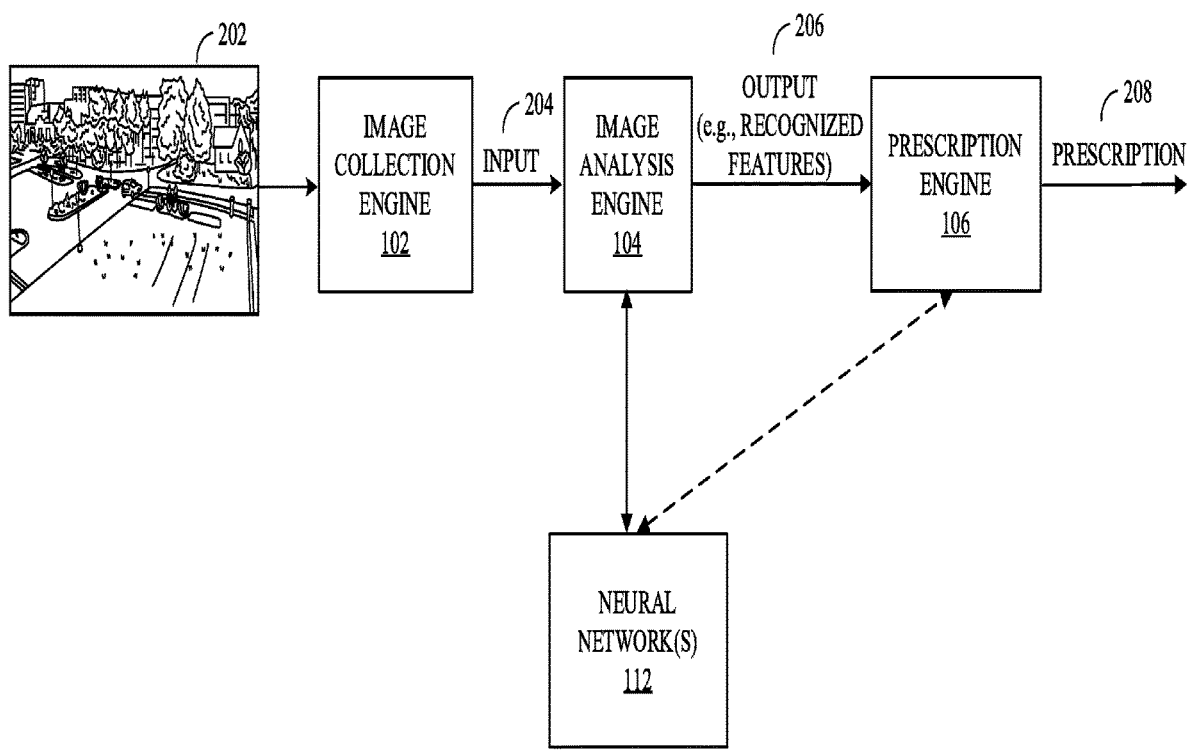
FIG. 2 illustrates an example flow for processing image data to identify environmental features and generate prescription measures.

FIG. 2 illustrates an example flow for processing image data to identify environmental features and generate prescription measures. In this example, image collection engine 102 obtains an image 202 of a specific geographic location, such as an urban neighborhood, a city, a town, or any other geographic region. The image collection engine 102 can obtain the image 202 from one or more sources, such as the Internet 120, data storage 116, a user (118), a remote server, an application, etc. For example, the image collection engine 102 can obtain the image 202 from a map or satellite application, such as GOOGLE STREET VIEW. As another example, the image collection engine 102 can obtain the image from one or more government sources, such as a city website or database. In some cases, the image collection engine 102 can obtain metadata of the image 202 and/or additional information about the location associated with the image 202, such as crime statistics, demographics data, landmark information, descriptive information, government-provided data and/or statistics, neighborhood data, etc.

The image 202 and any other data collected by the image collection engine 102 can be provided as input 204 to image analysis engine 104. Image analysis engine 104 can use the input 204 to identify environmental features in the image 202. For example, the image analysis engine 104 can use neural network 112 and computer vision technology to recognize objects in the image 202. For example, the image analysis engine 104 can analyze pixels and/or regions in the image 202 and intelligently recognize objects based on identified patterns and/or attributes.

The image analysis engine 104 can generate output 206 which can include recognized environmental features from the image 202. Prescription engine 106 can receive the output 206 from the image analysis engine 104 and use the recognized environmental features in the output 206 to generate a prescription 208. The prescription 208 can identify environmental features that may be implemented in the given location to improve the environment, human health and wellbeing, and/or healthcare costs associated with the environment. The prescribed environmental features can include environmental features known or believed to influence human health and wellbeing, such as greenery, benches, parks, sidewalks, bike paths, streetlights, access to sunlight, etc.

Figure 3:
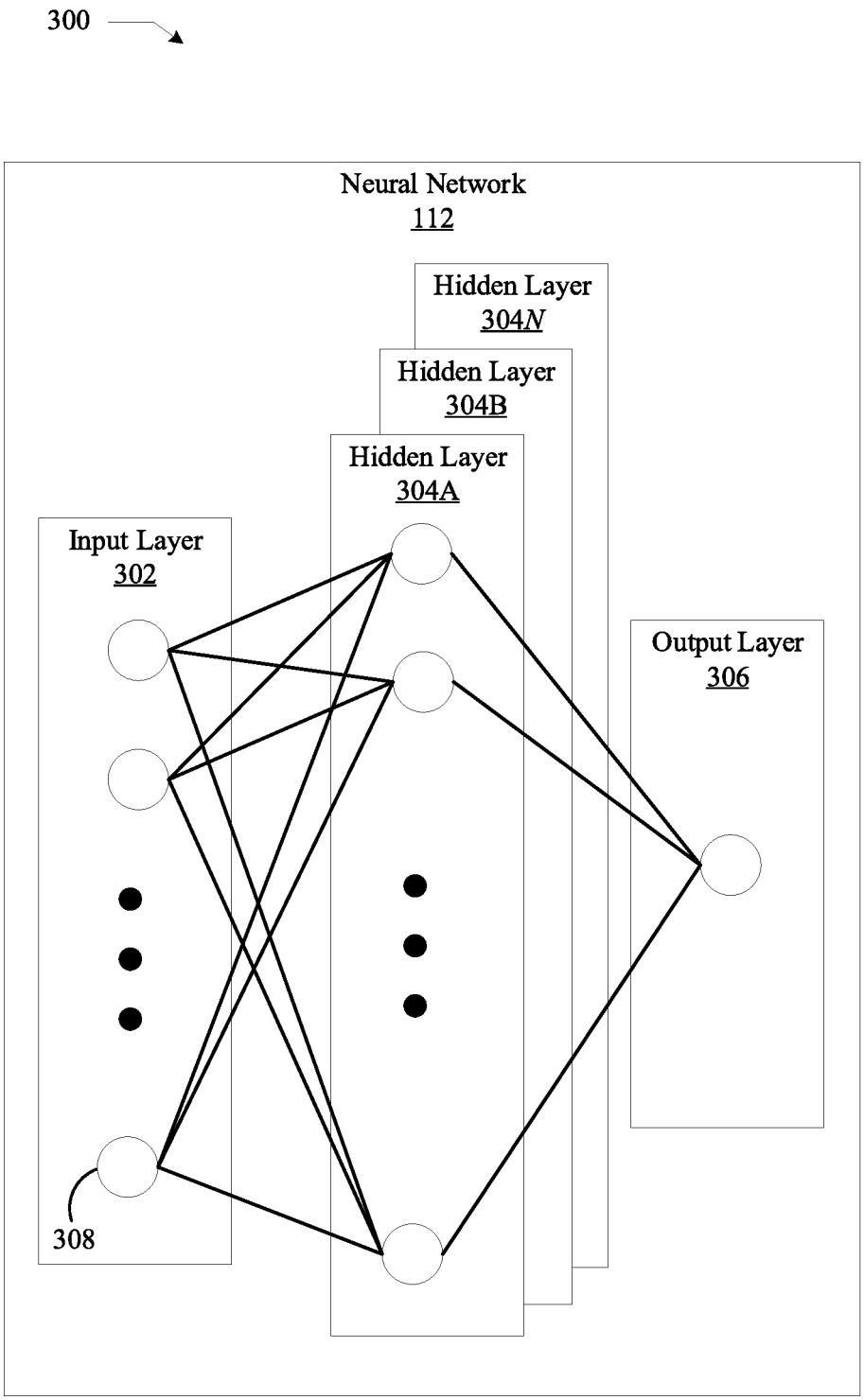
FIG. 3 illustrates an example configuration of a neural network as shown in FIG. 1.

FIG. 3 illustrates an example configuration 300 of neural network 112. In this example, the neural network 112 includes an input layer 302 which includes input data, such as collected images (e.g., image 202). In one illustrative example, the input layer 302 can include data representing the pixels of one or more input images.

The neural network 112 includes hidden layers 304A through 304N (collectively "304" hereinafter). The hidden layers 304 can include n number of hidden layers, where n is an integer greater than or equal to one. The number of hidden layers can be made to include as many layers as needed for the given application. The neural network 112 further includes an output layer 306 that provides an output resulting from the processing performed by the hidden layers 304. In one illustrative example, the output layer 306 can provide a classification and/or localization of one or more objects in an input image (e.g., 202). The classification can include a class identifying the type of object (e.g., a person, a dog, a cat, a car, a tree, a sidewalk, a bench, a lake, a house, a sunset, or any other object) and the localization can include a bounding box indicating the location of the object.

The neural network 112 is a multi-layer deep learning network of interconnected nodes. Each node can represent a piece of information. Information associated with the nodes is shared among the different layers and each layer retains information as information is processed. In some cases, the neural network 112 can include a feed-forward network, in which case there are no feedback connections where outputs of the network are fed back into itself. In some cases, the neural network 112 can include a recurrent neural network, which can have loops that allow information to be carried across nodes while reading in input.

Information can be exchanged between nodes through node-to-node interconnections between the various layers. Nodes of the input layer 302 can activate a set of nodes in the first hidden layer 304A. For example, as shown, each of the input nodes of the input layer 302 is connected to each of the nodes of the first hidden layer 304A. The nodes of the hidden layer 304A can transform the information of each input node by applying activation functions to the information. The information derived from the transformation can then be passed to and can activate the nodes of the next hidden layer (e.g., 304B), which can perform their own designated functions. Example functions include convolutional, up-sampling, data transformation, pooling, and/or any other suitable functions. The output of the hidden layer (e.g., 304B) can then activate nodes of the next hidden layer (e.g., 304N), and so on. The output of the last hidden layer can activate one or more nodes of the output layer 306, at which point an output is provided. In some cases, while nodes (e.g., node 308) in the neural network 112 are shown as having multiple output lines, a node has a single output and all lines shown as being output from a node represent the same output value.

In some cases, each node or interconnection between nodes can have a weight that is a set of parameters derived from the training of the neural network 112. For example, an interconnection between nodes can represent a piece of information learned about the interconnected nodes. The interconnection can have a numeric weight that can be tuned (e.g., based on a training dataset), allowing the neural network 112 to be adaptive to inputs and able to learn as more data is processed.

The neural network 112 can be pre-trained to process the features from the data in the input layer 302 using the different hidden layers 304 in order to provide the output through the output layer 306. In an example in which the neural network 112 is used to identify objects in images, the neural network 112 can be trained using training data that includes both images and labels. For instance, training images can be input into the neural network 112, with each training image having a label indicating the classes of the one or more objects in each image (basically, indicating to the network what the objects are and what features they have).

In some cases, the neural network 112 can adjust the weights of the nodes using a training process called backpropagation. Backpropagation can include a forward pass, a loss function, a backward pass, and a weight update. The forward pass, loss function, backward pass, and parameter update is performed for one training iteration. The process can be repeated for a certain number of iterations for each set of training images until the neural network 112 is trained enough so that the weights of the layers are accurately tuned.

For the example of identifying objects in images, the forward pass can include passing a training image through the neural network 112. The weights can be initially randomized before the neural network 112 is trained. The image can include, for example, an array of numbers representing the pixels of the image. Each number in the array can include a value from 0 to 255 describing the pixel intensity at that position in the array. In one example, the array can include a 28×28×3 array of numbers with 28 rows and 28 columns of pixels and 3 color components (such as red, green, and blue, or luma and two chroma components, or the like).

For a first training iteration for the neural network 112, the output can include values that do not give preference to any particular class due to the weights being randomly selected at initialization. For example, if the output is a vector with probabilities that the object includes different classes, the probability value for each of the different classes may be equal or at least very similar (e.g., for ten possible classes, each class may have a probability value of 0.1). With the initial weights, the neural network 112 is unable to determine low level features and thus cannot make an accurate determination of what the classification of the object might be. A loss function can be used to analyze errors in the output. Any suitable loss function definition can be used.

The loss (or error) can be high for the first training images since the actual values will be different than the predicted output. The goal of training is to minimize the amount of loss so that the predicted output is the same as the training label. The neural network 112 can perform a backward pass by determining which inputs (weights) most contributed to the loss of the network, and can adjust the weights so that the loss decreases and is eventually minimized.

A derivative of the loss with respect to the weights can be computed to determine the weights that contributed most to the loss of the network. After the derivative is computed, a weight update can be performed by updating the weights of the filters. For example, the weights can be updated so that they change in the opposite direction of the gradient. A learning rate can be set to any suitable value, with a high learning rate including larger weight updates and a lower value indicating smaller weight updates.

The neural network 112 can include any suitable deep network. One example includes a convolutional neural network (CNN), which includes an input layer and an output layer, with multiple hidden layers between the input and out layers. The hidden layers of a CNN include a series of convolutional, nonlinear, pooling (for downsampling), and fully connected layers. In other examples, the neural network 112 can represent any other deep network other than a CNN, such as an autoencoder, a deep belief nets (DBNs), a Recurrent Neural Networks (RNNs), etc.

Figure 4:
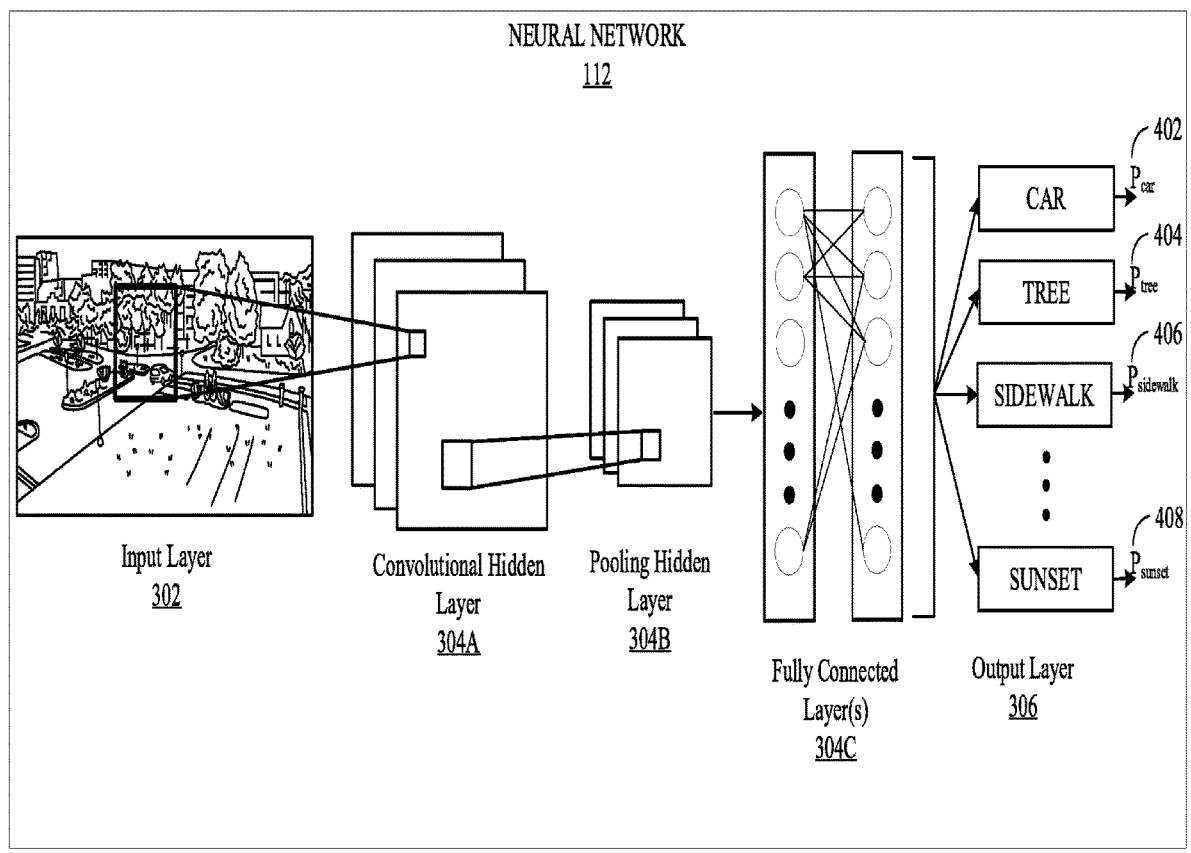
FIG. 4 illustrates an example use of a neural network as shown in FIG. 1, to perform deep learning.

FIG. 4 illustrates an example use of neural network 112 to perform deep learning. In this example, the neural network 112 includes an input layer 302, a convolutional hidden layer 304A, a pooling hidden layer 304B, fully connected layers 304C, and output layer 306. The neural network 112 can identify specific environmental features (e.g., house, shops, benches, trees, roads, sidewalks, bike paths, streetlights, etc.) in an image (e.g., 202). First, each pixel in the image is considered as a neuron that has learnable weights and biases. Each neuron receives some inputs, performs a dot product and optionally follows it with a non-linearity function. The neural network 112 can also encode certain properties into the architecture by expressing a single differentiable score function from the raw image pixels on one end to class scores at the other to extract specific environmental features from the target image. After identifying objects in the image as specific environmental features, the neural network 112 can generate a mean score (or z-score) of each feature and take the average of the scores within the user-defined buffer.

In some examples, the input layer 304A includes data representing an image (e.g., 202). For example, the data can include an array of numbers representing the pixels of the image, with each number in the array including a value from 0 to 255 describing the pixel intensity at that position in the array. The image can be passed through the convolutional hidden layer 304A, an optional non-linear activation layer, a pooling hidden layer 304B, and fully connected hidden layers 306 to get an output at the output layer 306. The outputs 402, 404, 406, 408 can indicate a class of an object (e.g., car, tree, sidewalk, sunset) or a probability of classes that best describes the objects in the image.

The convolutional hidden layer 304A can analyze the image data of the input layer 302A. Each node of the convolutional hidden layer 304A can be connected to a region of nodes (pixels) of the input image. The convolutional hidden layer 304A can be considered as one or more filters (each filter corresponding to a different activation or feature map), with each convolutional iteration of a filter being a node or neuron of the convolutional hidden layer 304A. Each connection between a node and a receptive field (region of nodes (pixels)) for that node learns a weight and, in some cases, an overall bias such that each node learns to analyze its particular local receptive field in the input image.

The convolutional nature of the convolutional hidden layer 304A is due to each node of the convolutional layer being applied to its corresponding receptive field. For example, a filter of the convolutional hidden layer 304A can begin in the top-left corner of the input image array and can convolve around the input image. As noted above, each convolutional iteration of the filter can be considered a node or neuron of the convolutional hidden layer 304A. At each convolutional iteration, the values of the filter are multiplied with a corresponding number of the original pixel values of the image. The multiplications from each convolutional iteration can be summed together to obtain a total sum for that iteration or node. The process is next continued at a next location in the input image according to the receptive field of a next node in the convolutional hidden layer 304A. Processing the filter at each unique location of the input volume produces a number representing the filter results for that location, resulting in a total sum value being determined for each node of the convolutional hidden layer 304A.

The mapping from the input layer 302 to the convolutional hidden layer 304A can be referred to as an activation map (or feature map). The activation map includes a value for each node representing the filter results at each locations of the input volume. The activation map can include an array that includes the various total sum values resulting from each iteration of the filter on the input volume. The convolutional hidden layer 304A can include several activation maps in order to identify multiple features in an image. The example shown in FIG. 4 includes three activation maps. Using three activation maps, the convolutional hidden layer 304A can detect three different kinds of features, with each feature being detectable across the entire image.

In some examples, a non-linear hidden layer can be applied after the convolutional hidden layer 304A. The non-linear layer can be used to introduce non-linearity to a system that has been computing linear operations.

The pooling hidden layer 304B can be applied after the convolutional hidden layer 304A (and after the non-linear hidden layer when used). The pooling hidden layer 304B is used to simplify the information in the output from the convolutional hidden layer 304A. For example, the pooling hidden layer 304B can take each activation map output from the convolutional hidden layer 304A and generate a condensed activation map (or feature map) using a pooling function. Max-pooling is one example of a function performed by a pooling hidden layer. Other forms of pooling functions be used by the pooling hidden layer 304B, such as average pooling or other suitable pooling functions. A pooling function (e.g., a max-pooling filter) is applied to each activation map included in the convolutional hidden layer 304A. In the example shown in FIG. 4, three pooling filters are used for the three activation maps in the convolutional hidden layer 304A.

The pooling function (e.g., max-pooling) can determine whether a given feature is found anywhere in a region of the image, and discard the exact positional information. This can be done without affecting results of the feature detection because, once a feature has been found, the exact location of the feature is not as important as its approximate location relative to other features. Max-pooling (as well as other pooling methods) offer the benefit that there are fewer pooled features, thus reducing the number of parameters needed in later layers.

The fully connected layer 304C can connect every node from the pooling hidden layer 304B to every output node in the output layer 306. The fully connected layer 304C can obtain the output of the previous pooling layer 304B (which should represent the activation maps of high-level features) and determine the features that correlate to a particular class. For example, the fully connected layer 304C layer can determine the high-level features that most strongly correlate to a particular class, and can include weights (nodes) for the high-level features. A product can be computed between the weights of the fully connected layer 304C and the pooling hidden layer 304B to obtain probabilities for the different classes.

In some examples, the output from the output layer 306 can include an n-dimensional vector, where n can include the number of classes that the program has to choose from when classifying the object in the image. Other example outputs can also be provided. Each number in the n-dimensional vector can represent the probability the object is of a certain class.

Figure 5:
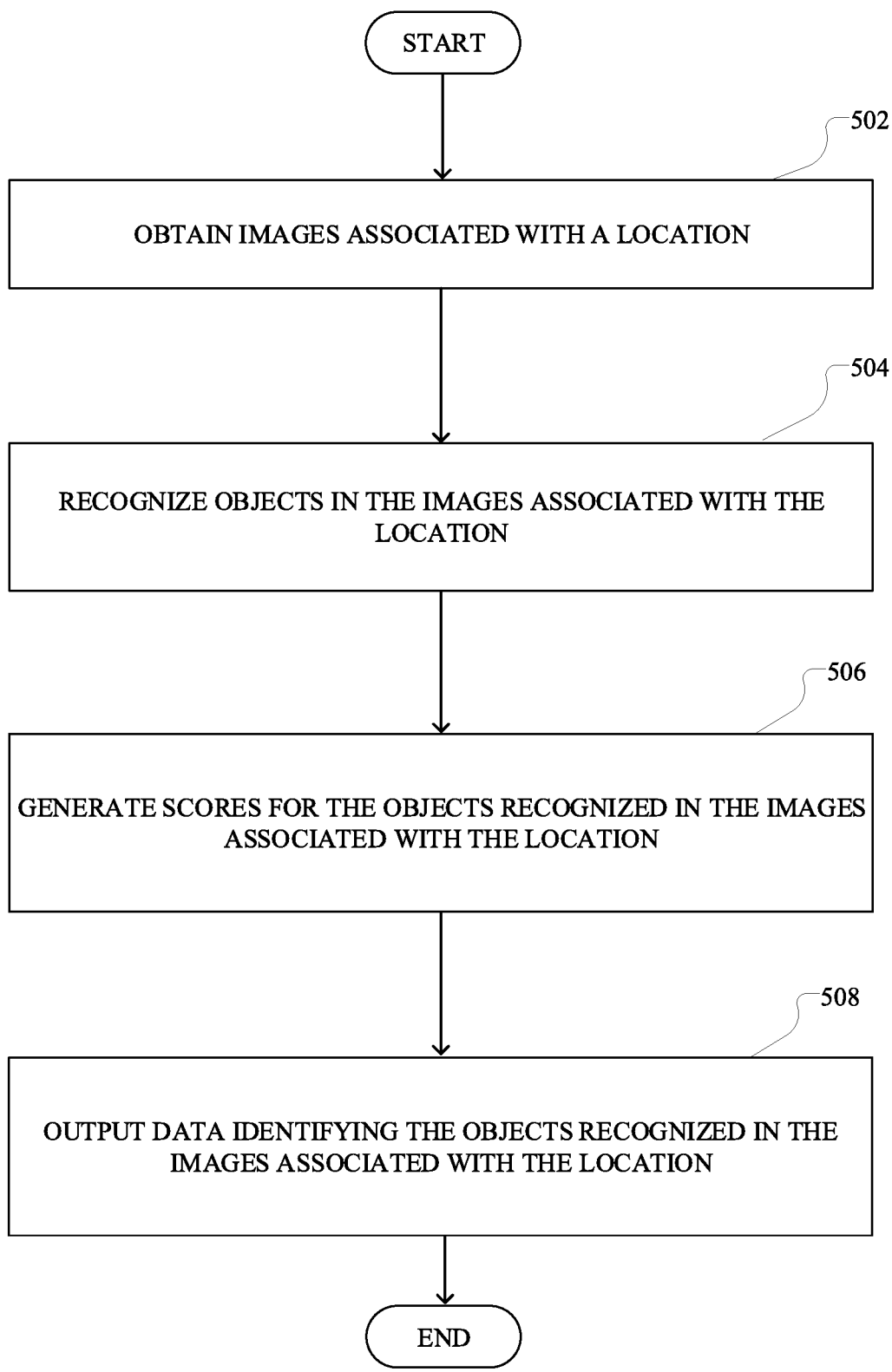
FIG. 5 illustrates an example method for implementing a computerized tool to automate an environmental auditing procedure.

FIG. 5 illustrates an example method for implementing a computerized tool to automate an environmental auditing procedure. The computerized tool can implement machine learning techniques to identify features in collected images. For example, the computerized tool can implement the neural network 112 as described in FIG. 4.

At step 502, the method obtains images associated with a location (e.g., a designated geographic area or within a user-selected buffer). In some cases, the method can collect images via the image collection engine 102. The image collection engine 102 can collect images from the Internet or any other source.

At step 504, the method can recognize objects in the images associated with the location. The method can recognize objects via the image analysis engine 104 and neural network 112 as previously described. For example, as previously described, the neural network 112 can identify specific environmental features (e.g., house, shops, benches, trees, roads, sidewalks, bike paths, streetlights, etc.) in an image (e.g., 202). First, each pixel in the image is considered as a neuron that has learnable weights and biases. Each neuron receives some inputs, performs a dot product and optionally follows it with a non-linearity function. The neural network 112 can also encode certain properties into the architecture by expressing a single differentiable score function from the raw image pixels on one end to class scores at the other to extract specific environmental features from the target image.

At step 506, the method can generate scores for the objects recognized in the images. For example, after identifying objects in an image as specific environmental features, the neural network 112 can generate a mean score (or z-score) of each feature and take the average of the scores.

At step 508, the method can output data (e.g., 402, 404, 406, 408) identifying the objects recognized in the images associated with the location. In some examples, the method can display the output data via a presentation engine (e.g., 114) on a display device.

Figure 6:
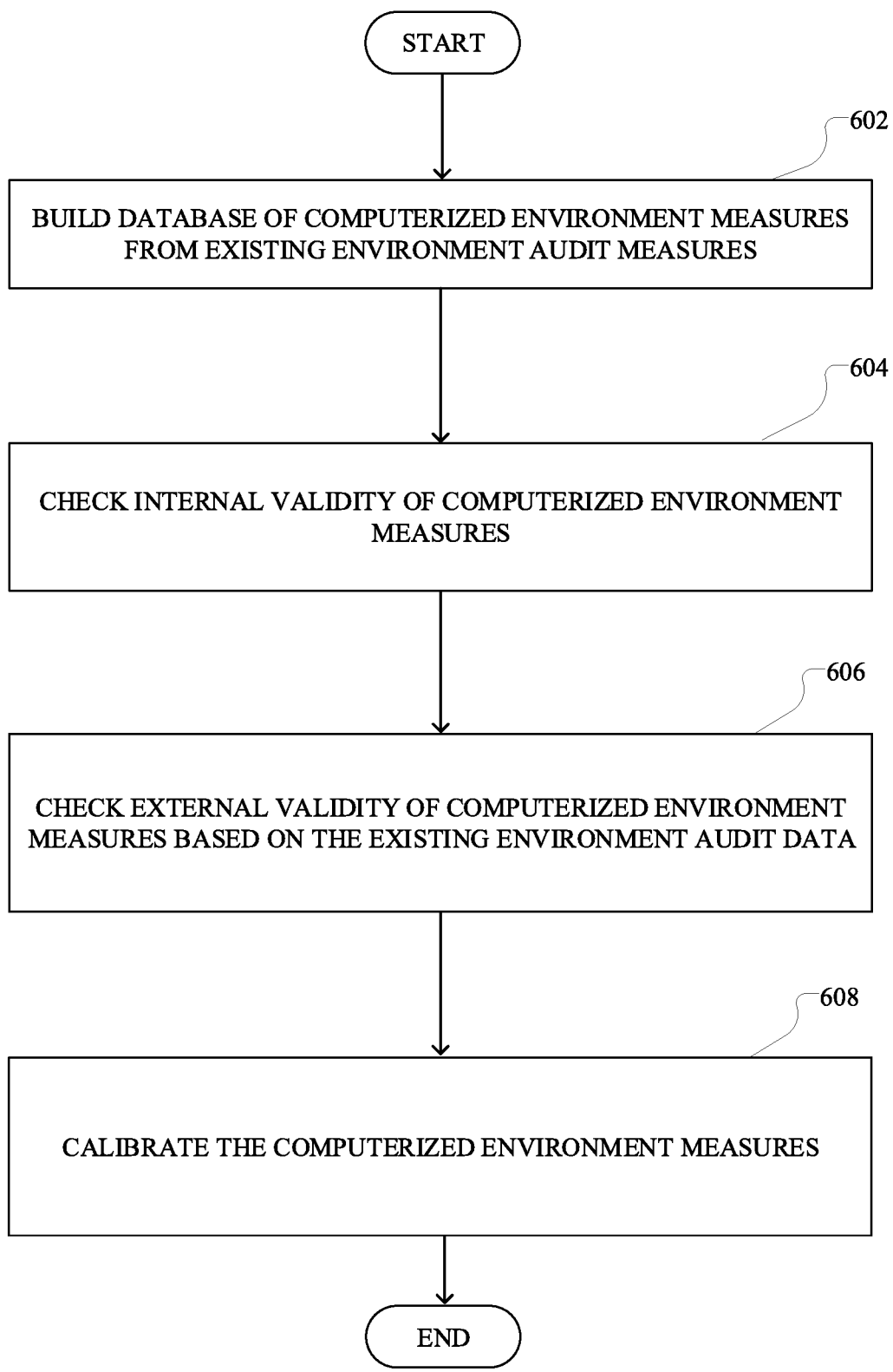
FIG. 6 illustrates an example method for validating and calibrating computerized measures generated in the example method shown in FIG. 5.

FIG. 6 illustrates an example method for validating and calibrating computerized measures generated in the example method shown in FIG. 5.

At step 602, the method can build a database of computerized environmental measures from existing environmental audit measures. At step 604, the method can check the internal validity of the computerized measures. In some cases, the method can check the internal validity by cross-validation.

At step 606, the method can check the external validity of the computerized measures based on the existing environmental audit data. For example, the method can check the external validity of the computerized measures by performing Pearson's correlation and k-Nearest Neighborhood likelihood computation against the original environmental audit measures.

At step 608, the method can calibrate the computerized measures by computing weights based on environmental audit measures from different countries, cities, age groups, etc. The computerized measures can thus be calibrated using actual measures as a reference.

Figure 7:
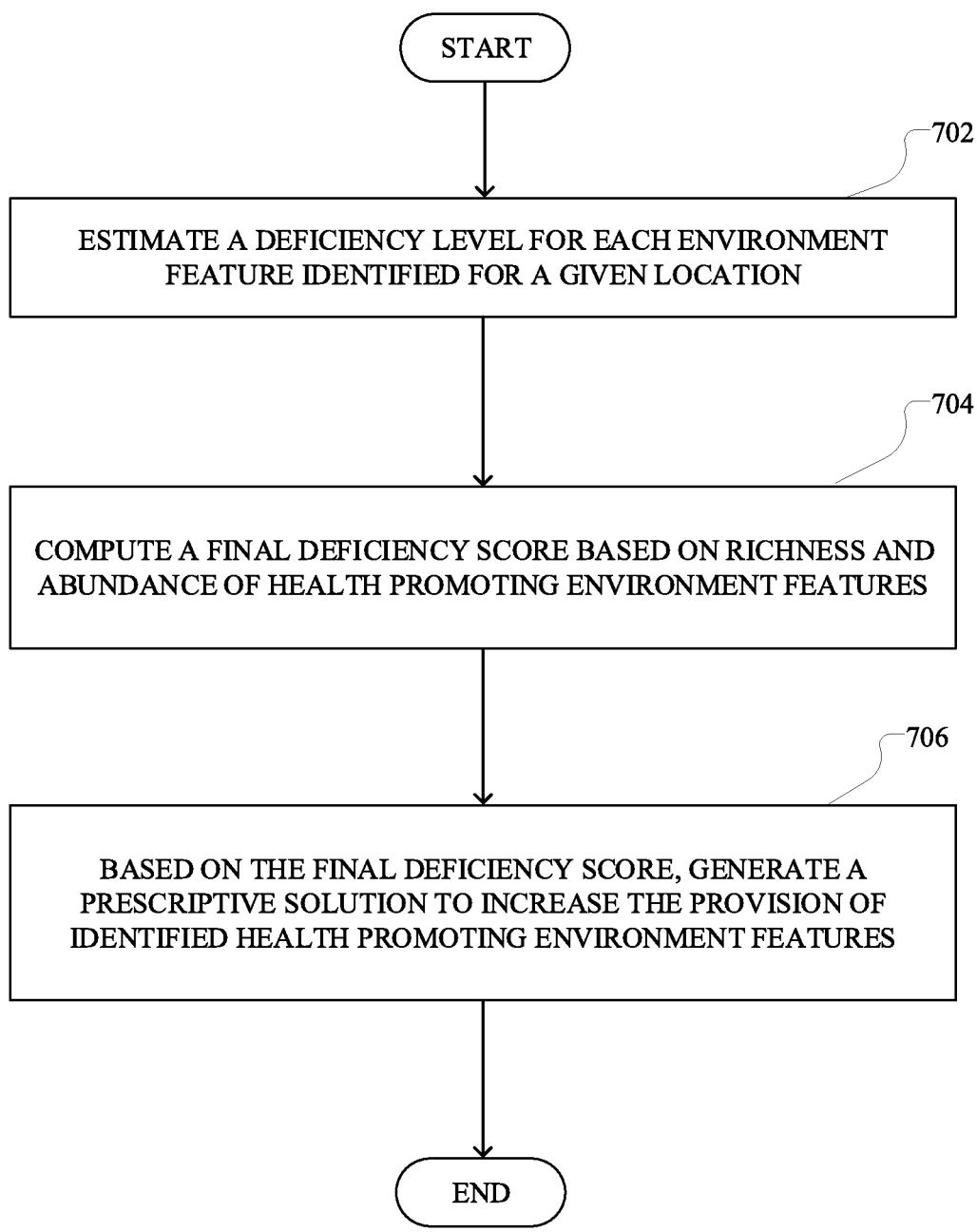
FIG. 7 illustrates an example method for implementing a prescriptive tool to improve environments for healthier living.

FIG. 7 illustrates an example method for implementing a prescriptive tool (e.g., prescriptive engine 106) to improve environments for healthier living.

At step 702, the method can estimate a deficiency level for each environmental feature identified for a given location (e.g., output features 402, 404, 406, 408). In some examples, the method can estimate a deficiency level for each identified environment feature known to enhance health and wellbeing, such as trees, benches, sidewalks, bike paths, streetlights, and etc. To estimate a deficiency level, the method can calculate an entropy index that can measure disorder or uncertainty.

At step 704, the method can compute a final deficiency score based on the richness and abundance of health-promoting environment features. In some examples, the final deficiency score can be computed as follows:

$$H = -\sum_{i=1}^{R} p_i \ln p_i$$

$$D = \frac{1}{\sum_{i=1}^{R} p_i^2}$$

Where, H refers to Shannon's entropy index, and D refers to Simpson's index. $p_i$ denotes the proportion of specific health-promoting environment feature i divided by the number of all environment features; R is the number of environment features. Both indices measure similar phenomenon, but Shannon's index is more affected by minor feature (richness) whereas Simpson's index gives more weight to dominant environment feature (abundance). Combination of the two indices gives a reliable measure of built environment richness and abundance.

In some examples, the method can combine and normalize the two indices, and convert the result into a percentage-based score to make it comparable across the database. The final deficiency score can be computed by subtracting the normalized percentage score from 100.

At step 706, the method can generate a prescriptive solution to increase the provision of identified health-promoting environment features based on the final deficiency score. In some examples, the suggested provision level can be estimated in percentage, and the method can display an appropriate recommendation. For example, the method can display "X % of more trees is needed to promote moderate-and-vigorous physical activity level by Y %". The provision level needed to achieve the desired level of health outcomes can be obtained by estimating pooled elasticity of certain environment features known to enhance health and wellbeing.

Figure 8:
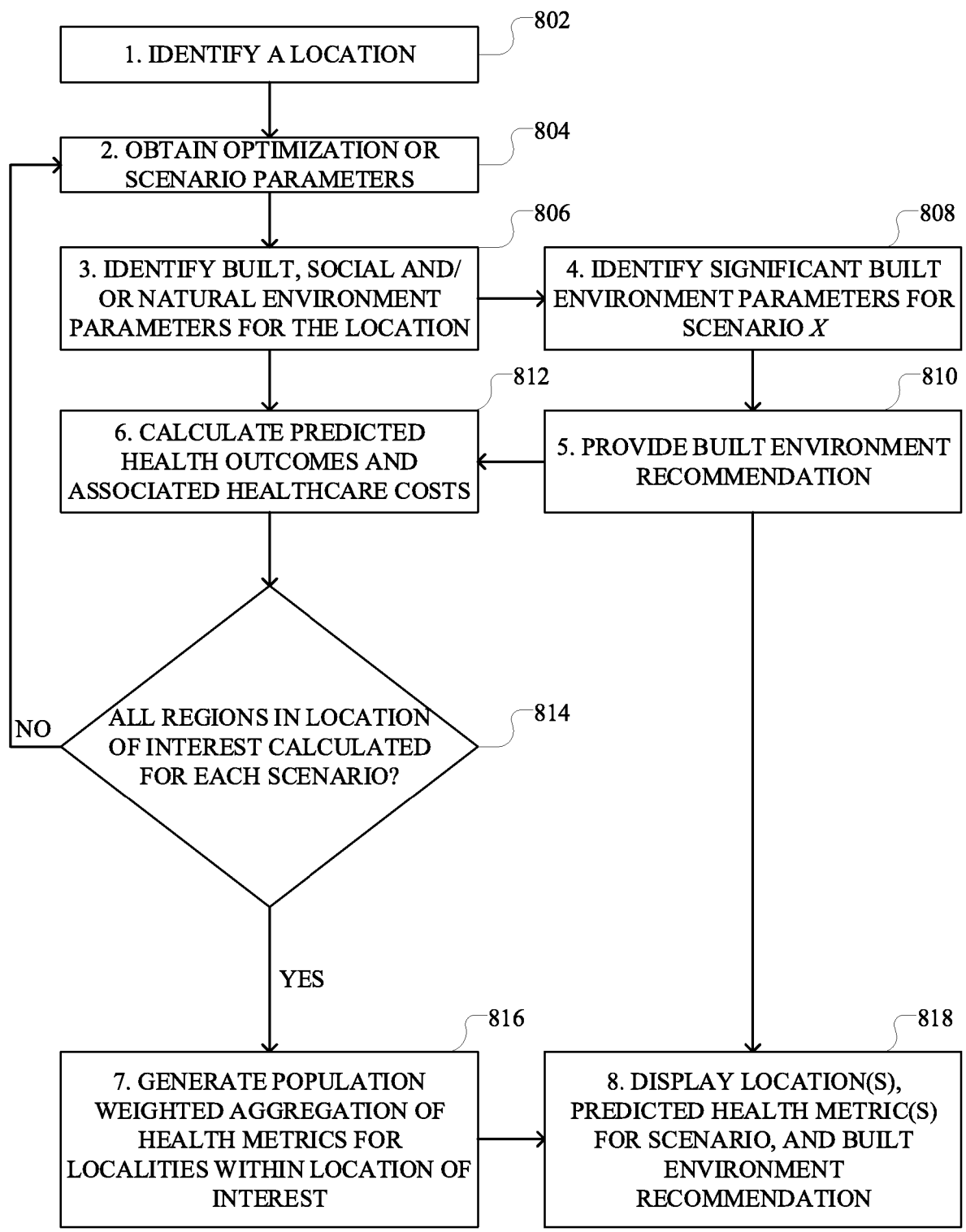
FIG. 8 illustrates a flow diagram of an example method for predicting health-related parameters for one or more environments and identifying changes to one or more environments that can be implemented to change a given health-related parameter.

FIG. 8 illustrates an example flow diagram for an example method to predict health-related outcomes or other metrics for one or more locations, and/or to identify changes to one or more environments that can be implemented to increase a given health-related outcome or other metric. For example, the flow diagram can represent a method for predicting location-based population health outcome from measures of built, natural, and/or social (e.g., demographic) environment parameters using a computing system such as system 100.

For the sake of clarity, the method is described in terms of system 100, as shown in FIG. 1, configured to practice the method. The steps outlined herein are exemplary and can be implemented in any combination thereof, including combinations that exclude, add, or modify certain steps.

In some examples, a user can supply hypothetical built environment changes and/or health-related outcomes that should be improved or maximized. For example, the disclosed method may model a proposed change to the built, social and/or natural environment of a given location (e.g., a "scenario") and calculate changes to one or more health-related outcomes that account for the variables modeled in the scenario.

In some aspects, the user may select a desired health-related outcome to decrease/increase (or minimize/maximize) and a system (100) implementing the present methods can be used to identify one or more recommended changes to the current built environment parameters that promote or optimize the user-selected health outcome. For example, a user may want to improve diabetes prevalence rates, and the present methods may suggest built environment changes that result in greater likelihood of exercise (e.g., by outputting proposed changes that increase the walkability of the location).

At Step 1 (block 802), a user may select, provide, or identify a location (e.g., a neighborhood in New York City).

In this example, at Step 2 (block 804), the user may specify one or more optimization preferences (e.g., improve/minimize diabetes prevalence rates). Optimization, in some aspects, may be determined by maximizing the difference between benefits and costs. In some aspects, a user may select one or more constraints (e.g., fiscal constraints) that should be accounted for in the optimization calculation. For example, a system (100) implementing the present methods may be used to select optimal built environment parameters for a given location that increase or maximize a desired a health outcome (e.g., a reduction in average body mass index (BMI)) to the extent possible while taking into account a budget constraint (e.g., a $10 million budget) and costs associated with various incremental built environment changes that may be potentially implemented (e.g., costs associated with creating a new intersection or train station, developing a bike path, etc.).

In still further aspects, optimization may take into account temporal restraints. For example, a user may be interested in determining the optimal built environment configuration that increases or maximizes a health outcome within a certain time period in order to accomplish near-term or long-term policy goals. Such calculations may include constraints related to temporal limitations, such as a predicted annual budget during the time period of interest and/or construction times associated with potential built environment changes (e.g., a new highway may require several years of development).

At Step 3 (block 806), built, natural and/or social (e.g., demographic) environment parameters may be identified or determined for the location selected at Step 1 (block 802) (e.g., internally by the tool discussed herein) and/or for a scenario (e.g., a scenario X provided by the user). For example, a user may provide or identify hypothetical built environment changes and/or health-related outcomes that may be improved or maximized. In some cases, the environment parameters can be identified using machine learning techniques as shown in FIG. 4.

At this stage, the method may proceed to either Step 4 (block 808) to perform optimization, or to Step 6 (block 812) to predict health outcomes without optimization.

At Step 4 (block 808), the system 100 can identify one or more built environment parameter(s) that have a significant impact on the desired health outcome for the user-selected scenario (e.g., the scenario X provided by the user at Step 3 (block 806)). In some aspects, the identification of significant built environment factors may take into account one or more of the social environment parameters associated with the location. In some aspects, only a single most significant built environment factor is identified. In others, any arbitrary cut-off may be implemented (e.g., the optimization routine may be limited to the five most significant built environment factors).

At Step 5 (block 810), the system 100 can use the significant built environment parameter(s) identified at Step 4 (block 808) to generate an optimal built environment (to the extent possible in view of any user-supplied or other constraints), which may be saved as another scenario (e.g., Scenario X-2). At this stage, the system 100 can display the optimal built environment as output (i.e., by proceeding to Step 8, block 818). Alternatively, the optimized scenario may be used as input for Step 6 (block 812).

At Step 6 (block 812), the system 100 can calculate predicted health outcomes (e.g., physical activity from travel and recreation, body-mass index (BMI), or other health outcomes) and associated healthcare costs from such outcomes using predictive equations. As illustrated by this example, the prediction may be based on the built, natural and/or social (e.g., demographic) environment parameters identified at Step 3 (block 806) (examples are shown in FIG. 9), or optimized at Step 5 (block 810).

The system 100 can analyze multiple locations within a larger region of interest (e.g., via system 100). In this case, at block 814, the method may include a step of determining whether all of the locations in a given region of interest have been calculated for the scenario. If so, the method may proceed to Step 7 (block 816). If not, the process may return to Step 2 (block 804).

At Step 7 (block 816), the system 100 can generate a population-weighted aggregation of health metrics for all locations within the region of interest. In some instances, this step may account for the relative population of a sub-area (e.g., a census block group) compared to the total population of the entire study area of interest (e.g., county).

Finally, at Step 8 (block 818), the system 100 can display the predicted health outcomes(s) for the location or for multiple locations and/or an entire region (e.g., via presentation engine 118). The predicted health outcomes may be for a current location, a given scenario for a location and/or optimized built environment parameters for the location, as discussed in the various aspects provided herein. The built environment recommendation for optimized locations or scenarios may be provided in a tabular form, a geographic form, or any other format.

To be clear, FIG. 8 represents an example aspect of the methods described herein. Other permutations that include some or all of these steps or other steps described herein may be implemented without departing from the spirit of the disclosure.

FIG. 9 illustrates a flow diagram illustrating additional details regarding Step 3 (block 806) and Step 6 (block 812) of FIG. 8, which relate to the identification of environmental parameters and prediction of a health outcome and associated healthcare costs for the location. For the sake of clarity, the steps in the flow diagram are described in terms of system 100, as shown in FIG. 1, configured to practice the steps. The steps outlined herein are exemplary and can be implemented in any combination thereof, including combinations that exclude, add, or modify certain steps.

At Step 3 (block 902), built, social, and/or natural environment parameters can be identified for a given location. In this particular example, the location is provided by the user at Step 1 (block 802) in FIG. 8.

At Step 3A (block 904), temporal characteristics of the scenario (e.g., provided by the user) can be determined.

At Step 3B (block 906 or block 908), if the scenario is a current condition, the system 100 can obtain parameters for the current condition. In some examples, the input environmental parameters can be pre-identified and/or calculated, or called from one or more internet sources in real time or near real time. Alternatively, if the scenario is a future condition or application, the system 100 obtains parameters for the future condition or application. In some examples, the environmental parameters here can be supplied by the user through a user interface and/or a third party scenario-planning tool.

At Step 3C (block 910), the system 100 can provide built, social, and/or natural environment parameters (e.g., via system 100) that may be used as inputs for Steps 6A, 6B, 6C and/or 6D (blocks 912, 914, 916 and/or 918). In some cases, the parameters can be unique or different for each block/step and health outcome.

At Step 6A (block 912), the system 100 can calculate a first predicted health outcome (e.g., expected physical activity for travel and recreation using predictive equations that may include built, social, and/or natural environment parameters from Step 3 (block 806) in FIG. 8).

At Step 6B (block 914), the system 100 can calculate a second predicted health outcome (e.g., predicted BMI using pre-determined predictive equations that may include physical activity from Step 6A (block 912) and one or more built, social, and/or natural environment parameters from Step 3 (block 806) in FIG. 8). Note that in this particular example, the second predicted health outcome is based on both environmental parameters and the associated predicted health outcome calculated at Step 6A (block 912). This step illustrates that in some cases, methods according to the disclosure may calculate a plurality of predicted health outcomes wherein some predicted health outcomes are used as intermediates to calculate additional predicted health outcomes by leveraging data (e.g., positive or negative correlations) between various predicted health outcomes.

At Step 6C (block 916), the system 100 can calculate predicted health metrics using pre-determined predictive equations that may include one or more previously-determined predicted health outcomes. In this example, physical activity (calculated at Step 6A, block 912), BMI (calculated at Step 6B, block 914), and one or more built, social, and/or natural environment parameters from Step 3 (block 806) in FIG. 8 can be leveraged to arrive at a third predicted health metric.

At Step 6D (block 918), the system 100 can calculate predicted healthcare costs based on the one or more previously-determined predicted health outcomes. In this example, physical activity (calculated at Step 6A, block 912), BMI (calculated at Step 6B, block 914), predicted health metrics (calculated at Step 6C, block 916) and one or more built, social, and/or natural environment parameters from Step 3 (block 806) in FIG. 8 can be leveraged to arrive at predicted healthcare costs.

In some aspects, methods in accordance with this aspect of the disclosure may output a final predicted health outcome, a plurality of predicted health outcomes (e.g., displaying various intermediary predicted health outcomes as illustrated by FIG. 9), and/or predicted healthcare costs. It is understood that this configuration may be generalized to any of the alternative exemplary aspects described herein.

Example Implementation

Step 1. The following hypothetical provides an illustrative and non-limiting example of a method according to the disclosure used in one example context. Assume that a city planner wishes to understand the health impacts of a proposal to redevelop a location is interested in understanding how to best improve the health of the residents of the location while redeveloping a large number of parcels. The city planner, having access to scenario planning tool (e.g., system 100) implementing an aspect of the disclosure, may provide the tool (e.g., 100) with the geographic boundaries of the location of interest. The tool (100) in turn may present a list of built environment, natural environment, and social environment parameters to the city planner (hereinafter, "user") that could potentially be changed. The tool (100) may have this data stored locally or may have downloaded it from a remote database in response to the user's identification of the location of interest.

The user may then choose, for example, population density, household income, land use mix—including types residential housing, commercial space, and green space—and employment density, as environmental parameters of interest. The tool (100) may then, accordingly, provide current conditions for each user-selected environmental parameter and associated health metrics of interest. In this example, a feature of this and subsequent steps is that the spatial variation in both environmental parameters and health metrics within the area of interest would be displayed in a map as illustrated in FIG. 10. Tabular and graphical representations of the data may also be provided to show indicators for the entire area and the variation within the area.

Step 2. The next step is defining the proposed changes to the area. In user-defined mode, the tabular, graphical, and mapping process in Step 1 supports the user in defining and refining a proposal. Within the tool (100), the user can define proposed new levels of population density, household income, land use mix, and employment density. For example, this could be done by inputting numerical levels or by indicating a percent change for each factor.

Step 3. Upon defining the elements of their proposal in Step 2, the tool (100) may then provide in real time projected health and economic metrics. Metrics would be available at both fine-scale geography and full area aggregation. Presentation of the results may be provided in map form to understand spatial variation and in tabular and graphical form to understand larger area averages.

Step 4. Additionally, the tool (100) may display the change in health metrics and the monetized healthcare benefits associated with that change. For example, if the diabetes prevalence rate is currently 8% and, with the changes in the levers projected to be reduced to 7%, then the tool (100) may present the difference in prevalence rates (1%), the number of diabetes cases avoided, and the healthcare costs avoided from implementing the proposal.

The process defined in Steps 2-4, could be repeated in rapid succession, allowing the user to efficiently review the health and economic implications of various combinations of environmental factors.

In another example aspect, the tool (100) could provide pre-packaged baskets of environmental changes. For example, it might have multiple choices such as "compact urban core", "standard suburban", or "compact suburban" that would pre-package definitions required in Step 2.

In another embodiment, the user could select a "goal mode" instead of Step 2. The user would then be prompted to choose the health outcome or other metric upon to optimize. For example, the user could choose to reduce hypertension rates by 3%. Using only the environment parameters selected in Step 1, the software would calculate combinations and levels of increased population density, household income types, land use mix, and employment density to meet the goal. The tool (100) would display the spatial variation of the factors in map form as well as aggregated change in tabular and graphical form. It may also display additional predicted health outcomes such as incidence of diabetes or economic metrics such as decreased healthcare cost or fewer days of missed work.

In another example aspect, the user could select "optimization mode" instead of Step 2. This mode would prompt the user to assign practical ranges and expense associated with the environmental parameters chosen within Step 1. For example, if in Step 1 the user selected bicycle and pedestrian facilities, this mode would ask about the density or length of various facility types and the associated cost with each. The tool (100), using the predicted health outcomes and associated economic metrics could then propose a combination of facilities that maximize the difference between cost of implementing the facilities and healthcare cost benefits.

It is expressly understood that the preceding example, and variants thereof, are non-limiting and provided solely to illustrate potential implementations of the methods described herein.

While, for purposes of simplicity of explanation, the methods discussed herein are shown and described as a series of acts, it is to be understood and appreciated that the methods (and further methods related thereto) are not limited by the order of acts, as some acts may, in accordance with one or more aspects, occur in different orders and/or concurrently with other acts from that shown and described herein. For example, it is to be appreciated that a method could alternatively be represented as a series of interrelated states or events, such as in a state diagram. Moreover, not all illustrated acts may be required to implement a method in accordance with one or more features described herein.

It is to be understood that the specific order or hierarchy of steps in the methods disclosed is an illustration of example processes. Based upon design or implementation preferences, it is understood that the specific order or hierarchy of steps in the methods may be rearranged. The accompanying method claims present elements of the various steps in a sample order, and are not meant to be limited to the specific order or hierarchy presented unless specifically recited therein.

FIG. 10 illustrates an example display 1000 depicting a map 1002 and spatial variations in environmental parameters 1006 and health metrics 1008 within an area of interest. The area of interest is represented by the map 1002. The map 1002 can be coded (e.g., based on colors, patterns, labels, etc.) to display a distribution of prevalence rates 1004, such as obesity prevalence rates. The display 1000 can present specific environmental parameters 1006 as inputs for ascertaining specific health metrics 1008 or outcomes as output.

It should be noted that the environmental parameters 1006 and health metrics 1008 in display 1000 are non-limiting examples provided for explanation purposes. Other amounts and/or types of environmental parameters and health metrics can be presented in display 1000 depending on the specific implementation and preferences. Moreover, other formats for displaying the location depicted by map 1002, the environmental parameters 1006, and/or the health metrics 1008 are also contemplated herein. For example, environmental parameters, location information, prevalence rates, healthcare costs, health outcomes, etc., can be formatted in tabular form, in chart or graph form, and/or any other textual and/or graphical form.

The disclosure now turns to FIG. 11 which illustrates an example computing system architecture 1100 including components in electrical communication with each other using a connection 1105, such as a bus. System 1100 includes a processing unit (CPU or processor) 1110 and a system connection 1105 that couples various system components including the system memory 1115, such as read only memory (ROM) 1120 and random access memory (RAM) 1125, to the processor 1110. The system 1100 can include a cache of high-speed memory connected directly with, in close proximity to, or integrated as part of the processor 1110. The system 1100 can copy data from the memory 1115 and/or the storage device 1130 to the cache 1112 for quick access by the processor 1110. In this way, the cache can provide a performance boost that avoids processor 1110 delays while waiting for data. These and other modules can control or be configured to control the processor 1110 to perform various actions. Other system memory 1115 may be available for use as well. The memory 1115 can include multiple different types of memory with different performance characteristics. The processor 1110 can include any general purpose processor and a hardware or software service, such as service 1 1132, service 2 1134, and service 3 1136 stored in storage device 1130, configured to control the processor 1110 as well as a special-purpose processor where software instructions are incorporated into the actual processor design. The processor 1110 may be a completely self-contained computing system, containing multiple cores or processors, a bus, memory controller, cache, etc. A multi-core processor may be symmetric or asymmetric.

To enable user interaction with the computing device 1100, an input device 1145 can represent any number of input mechanisms, such as a microphone for speech, a touch-sensitive screen for gesture or graphical input, keyboard, mouse, motion input, speech and so forth. An output device 1135 can also be one or more of a number of output mechanisms known to those of skill in the art. In some instances, multimodal systems can enable a user to provide multiple types of input to communicate with the computing device 1100. The communications interface 1140 can generally govern and manage the user input and system output. There is no restriction on operating on any particular hardware arrangement and therefore the basic features here may easily be substituted for improved hardware or firmware arrangements as they are developed.

Storage device 1130 is a non-volatile memory and can be a hard disk or other types of computer readable media which can store data that are accessible by a computer, such as magnetic cassettes, flash memory cards, solid state memory devices, digital versatile disks, cartridges, random access memories (RAMs) 1125, read only memory (ROM) 1120, and hybrids thereof.

The storage device 1130 can include services 1132, 1134, 1136 for controlling the processor 1110. Other hardware or software modules are contemplated. The storage device 1130 can be connected to the system connection 1105. In one aspect, a hardware module that performs a particular function can include the software component stored in a computer-readable medium in connection with the necessary hardware components, such as the processor 1110, connection 1105, output device 1135, and so forth, to carry out the function.

For clarity of explanation, in some instances the present technology may be presented as including individual functional blocks including functional blocks comprising devices, device components, steps or routines in a method embodied in software, or combinations of hardware and software.

In some embodiments the computer-readable storage devices, mediums, and memories can include a cable or wireless signal containing a bit stream and the like. However, when mentioned, non-transitory computer-readable storage media expressly exclude media such as energy, carrier signals, electromagnetic waves, and signals per se.

Methods according to the above-described examples can be implemented using computer-executable instructions that are stored or otherwise available from computer readable media. Such instructions can comprise, for example, instructions and data which cause or otherwise configure a general purpose computer, special purpose computer, or special purpose processing device to perform a certain function or group of functions. Portions of computer resources used can be accessible over a network. The computer executable instructions may be, for example, binaries, intermediate format instructions such as assembly language, firmware, or source code. Examples of computer-readable media that may be used to store instructions, information used, and/or information created during methods according to described examples include magnetic or optical disks, flash memory, USB devices provided with non-volatile memory, networked storage devices, and so on.

Devices implementing methods according to these disclosures can comprise hardware, firmware and/or software, and can take any of a variety of form factors. Typical examples of such form factors include laptops, smart phones, small form factor personal computers, personal digital assistants, rackmount devices, standalone devices, and so on. Functionality described herein also can be embodied in peripherals or add-in cards. Such functionality can also be implemented on a circuit board among different chips or different processes executing in a single device, by way of further example.

The instructions, media for conveying such instructions, computing resources for executing them, and other structures for supporting such computing resources are means for providing the functions described in these disclosures.

Although a variety of examples and other information was used to explain aspects within the scope of the appended claims, no limitation of the claims should be implied based on particular features or arrangements in such examples, as one of ordinary skill would be able to use these examples to derive a wide variety of implementations. Further and although some subject matter may have been described in language specific to examples of structural features and/or method steps, it is to be understood that the subject matter defined in the appended claims is not necessarily limited to these described features or acts. For example, such functionality can be distributed differently or performed in components other than those identified herein. Rather, the described features and steps are disclosed as examples of components of systems and methods within the scope of the appended claims.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but is to be accorded the full scope consistent with the language of the claims, wherein reference to an element in the singular is not intended to mean "one and only one" unless specifically so stated, but rather "one or more." Unless specifically stated otherwise, the term "some" refers to one or more. A phrase referring to "at least one of" a list of items in the claims and/or specification refers to any combination of those items, including single members or multiple members. As an example, "at least one of a, b, and c" is intended to cover a; b; c; a and b; a and c; b and c; or a, b and c.

What is claimed is:

1. A computer-implemented method comprising:
   receiving a request to predict one or more health metrics of a population associated with a location;
   acquiring at least one image of the location via a network, by one or more processors;
   identifying a plurality of built environment micro scale parameters associated with the location, based on analysis of pixels of the at least one image of the location using computer vision and a machine learning tool, by the one or more processors, to classify an object in the at least one image in one of a number n classes of the built environment micro scale parameters, wherein an output of the machine learning tool includes at least one n-dimensional vector, where each number in the at least one n-dimensional vector represents a probability that the object is of a certain class;
   calculating, via the one or more processors, a quantitative measure of at least one predicted health metric of the population associated with the location based on a characteristic of at least one of the plurality of the identified built environment micro scale parameters associated with the location using at least one predictive equation correlating the characteristic of the identified built environment micro scale parameter with the one or more predicted health metrics; and
   displaying, via the one or more processors, the at least one predicted health metric associated with the location.

2. The method of claim 1, further comprising:
   receiving input comprising at least one new or modified built environment micro scale parameter associated with the location, selected by a user;
   calculating one or more predicted health metrics associated with the location based on the at least one new or modified built environment micro scale parameter;
   calculating one or more economic benefits resulting from a change in the predicted health metrics associated with the location, based upon the new or modified built environment micro scale parameter; and
   presenting the one or more economic benefits.

3. The method of claim 2, further comprising:
   receiving input comprising at least one of a cost associated with the at least one new or modified built environment micro scale parameter and an estimated change in health care costs resulting from changes in the one or more predicted health metrics associated with the location as a result of the at least one new or modified built environment micro scale parameter; and
   displaying, via the one or more processors, one or more costs or benefits resulting from the at least one new or modified built environment micro scale parameter.

4. The method of claim 2, wherein the at least one new or modified built environment micro scale parameter comprises:
   a presence or absence of street lights, benches, curb cuts at intersections, traffic signals, and/or marked crosswalks;
   a width, condition and/or continuity of a sidewalk;
   a distance from a sidewalk;
   a height of a building;
   a presence and/or location of windows on a building;
   a width of an intersection crossing;
   a road between intersections; and/or
   a pedestrian environment.

5. The method of claim 1, wherein the location comprises at least one of a census block group, a neighborhood, a borough, and a precinct, the method further comprising:
   calculating a population-weighted aggregation of predicted health metrics for at least one of:
      the census block group, the neighborhood, the borough, or the precinct;
      a subset of the neighborhood, the borough, or the precinct; and
      a user-selected subset of the neighborhood, borough, or precinct; and
   displaying, the population-weighted aggregation of predicted health metrics.

6. The method of claim 1, wherein the at least one predicted health metric for the population associated with the location comprises at least one of:
   physical activity;
   body mass index;
   rate of obesity; and
   at least one health outcome, wherein the health outcome comprises a likelihood to have at least one of a cardiovascular disease, hypertension, type-2 diabetes, and/or a mental health issue;
   wherein the predicted health metric is a mean or median value for a typical resident or a subpopulation of the location.

7. The method of claim 1, wherein the built environment micro scale parameter comprises a parameter associated with:
   a presence or absence of street lights, benches, curb cuts at intersections, traffic signals, and/or marked crosswalks;
   a width, condition and/or continuity of a sidewalk;
   a distance from a sidewalk;
   a height of a building;
   a presence and/or location of windows on buildings;
   a width of intersection crossings;
   a road between intersections; and/or
   pedestrian environment.

8. The method of claim 1 further comprising:
identifying a social environment parameter comprising at least one of:
gender;
race/ethnicity;
age;
number of vehicles owned per household;
income; and
housing and transportation costs per year per household; and
calculating, via the one or more processors, one or more predicted health metrics associated with the location based on the social environment parameter and the characteristic of the identified built environment micro scale parameter associated with the environment.

9. The method of claim 1, further comprising:
identifying a natural environment parameter, associated with the location, from the at least one image of the location using computer vision and a machine learning tool, the natural environment parameter comprising:
an area of developed open space in the location;
a percent land area with tree canopy coverage in the location;
ozone concentration in the location; and/or
a distance to parks from the location; and
calculating, via the one or more processors, one or more predicted health metrics associated with the location based on the natural environment parameter and the characteristic of the identified built environment micro scale parameter associated with the location.

10. The method of claim 2, further comprising:
calculating one or more predicted health metrics of the population associated with the location based on the at least one new or modified built environment micro scale parameter; and
calculating one or more economic benefits resulting from a change in the predicted health metrics associated with the location, based upon the at least one new or modified built environment micro scale parameter,
wherein the one or more economic benefits comprise at least one of direct, indirect, and induced health effects predicted by at least one of:
an econometric analysis;
a cost-of-illness calculation that accounts for direct health care costs and indirect productivity costs;
input-output modeling;
a value of statistical life methodology; and
directly measured relationships between built environment micro scale parameter and health care or productivity costs.

11. The method of claim 10, further comprising:
receiving the at least one new or modified built environment micro scale parameters selected by a user;
generating at least one scenario comprising a model of the location based upon the new or modified built environment micro scale parameters selected by the user;
calculating one or more new predicted health metrics associated with the location modeled in the scenario; and
displaying the one or more new predicted health metrics associated with the population of the location modeled in the scenario.

12. The method of claim 11, further comprising:
calculating one or more economic benefits resulting from changes to the one or more new predicted health metrics associated with the location modeled in the scenario; and
displaying at least one of a cost and benefit associated with the location based upon a user-provided budget to fund the new or modified built environment micro scale parameters, and an estimated change in health care costs resulting from changes in the one or more new predicted health metrics associated with the location modeled in the scenario.

13. The method of claim 1, wherein the health metric is a human health metric.

14. The method of claim 2, further comprising receiving a second input comprising at least one new or modified other built environment parameter associated with the location, selected by a user.

15. The method of claim 1, further comprising:
calculating a quantitative measure of at least one predicted health metric based on at least one other built environment parameter.

16. The method of claim 15, wherein the at least one other built environment parameter is:
residential density;
intersection density;
retail floor area ratio;
land use mix;
transit proximity;
walkability metric;
street connectivity; and/or
regional accessibility.

17. A non-transitory computer-readable medium storing computer-executable instructions which, when executed by one or more processors, cause the one or more processors to:
estimate coefficients of statistical correlations between health metrics of a population and at least one built environment micro scale parameter, via the one or more processors;
receive a request to predict one or more health metrics of a population associated with a location;
acquire at least one image of the location, by one or more processors;
identify a built environment micro scale parameter associated with the location, based on analysis of pixels of the at least one image of the location using computer vision and machine learning tool using a multi-layer deep learning neural network of interconnected nodes, by the one or more processors, trained using training images including labels indicating the classes of the one or more objects in each image;
calculate one or more predicted health metrics of the population associated with the location based on the at least one predictive equation, via the one or more processors; and
display the one or more predicted health metrics associated with the location.

18. The non-transitory computer-readable medium of claim 17, storing additional computer-executable instructions which, when executed by the one or more processors, cause the one or more processors to:
receive input comprising at least one new or modified built micro scale environment parameter associated with the location;
calculate one or more new predicted health metrics of the population associated with the location based on the at least one new or modified built environment micro scale parameter;
calculate one or more economic benefits resulting from a change between the one or more predicted health metrics and the one or more new predicted health metrics associated with the location; and
present the one or more economic benefits.

19. The non-transitory computer-readable medium of claim 18, storing additional computer-executable instructions which, when executed by the one or more processors, cause the one or more processors to:

receive input comprising at least one of a cost associated with the at least one new or modified built environment micro scale parameter and an estimated change in health care costs resulting from changes in the one or more predicted health metrics associated with the location as a result of the at least one new or modified built environment micro scale parameter; and display one or more costs or benefits resulting from the at least one new or modified bulk environment micro scale parameter.

20. The non-transitory computer-readable medium of claim 17, storing additional computer-executable instructions which, when executed by the one or more processors, cause the one or more processors to:

estimate coefficients of statistical correlations between health metrics of a population and built environment parameters, wherein the built environment parameters include a built environment micro scale parameter and at least one other built environment parameter.

21. The method of claim 20, wherein the at least one other built environment parameter is:
residential density;
intersection density;
retail floor area ratio;
land use mix;
transit proximity;
walkability metric;
street connectivity; and/or
regional accessibility.

* * * * *